(12) United States Patent
Fetissov et al.

(10) Patent No.: US 11,389,489 B2
(45) Date of Patent: *Jul. 19, 2022

(54) PHARMACEUTICAL AND FOOD COMPOSITIONS FOR INDUCING SATIATION AND PROLONGING SATIETY IN SUBJECTS IN NEED THEREOF

(71) Applicants: INSERM (INSTITUT NATIONAL DE LA SANTÉ ET DE LA RECHERCHE MÉDICALE), Paris (FR); CENTRE HOSPITALIER UNIVERSITAIRE DE ROUEN, Rouen (FR); UNIVERSITÉ DE ROUEN, Mont-Saint-Aignan (FR); TARGEDYS, Rouen (FR)

(72) Inventors: Serguei Fetissov, Rouen (FR); Pierre Dechelotte, Paris (FR); Jonathan Breton, Rouen (FR); Gregory Lambert, Rouen (FR); Naouel Tennoune, Rouen (FR); Romain Legrand, Rouen (FR)

(73) Assignees: INSERM (INSTITUT NATIONAL DE LA SANTE ET DE LA RECHERCHE MEDICALE), Paris (FR); CENTRE HOSPITALIER UNIVERSITAIRE DE ROUEN, Rouen (FR); UNIVERSITE DE ROUEN, Mont-Saint-Aignan (FR); TARGEDYS, Rouen (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/895,460

(22) Filed: Jun. 8, 2020

(65) Prior Publication Data

US 2020/0297783 A1 Sep. 24, 2020

Related U.S. Application Data

(63) Continuation of application No. 15/516,040, filed as application No. PCT/IB2015/001126 on Jun. 5, 2015, now abandoned.

(30) Foreign Application Priority Data

Oct. 2, 2014 (EP) .................................. 14306552

(51) Int. Cl.
  *A61K 35/741* (2015.01)
  *A61K 35/74* (2015.01)
  *A61K 38/16* (2006.01)
  *A23L 33/00* (2016.01)
  *A23L 33/135* (2016.01)
  *A61K 9/00* (2006.01)
  *A61P 3/04* (2006.01)

(52) U.S. Cl.
  CPC .......... *A61K 35/741* (2013.01); *A23L 33/135* (2016.08); *A23L 33/30* (2016.08); *A61K 9/0095* (2013.01); *A61K 35/74* (2013.01); *A61K 38/164* (2013.01); *A61P 3/04* (2018.01); *A23V 2002/00* (2013.01); *A23V 2200/3202* (2013.01); *A23V 2200/3204* (2013.01); *A23V 2200/332* (2013.01)

(58) Field of Classification Search
  CPC ... A23L 33/135; A23L 33/30; A23V 2002/00; A23V 2200/3202; A23V 2200/3204; A23V 2200/332; A61K 35/74; A61K 35/741; A61K 38/164; A61K 9/0095; A61P 3/04
  USPC ............. 435/69.1, 252.1; 514/10.7; 424/93.2
  See application file for complete search history.

(56) References Cited

U.S. PATENT DOCUMENTS

| | | | | |
|---|---|---|---|---|
| 10,682,389 | B2 * | 6/2020 | Fetissov | A23L 33/30 |
| 10,729,770 | B2 * | 8/2020 | Fetissov | A61P 1/14 |
| 10,888,592 | B2 * | 1/2021 | Fetissov | A61K 9/0095 |
| 2009/0311744 | A1 * | 12/2009 | DeFrees | C12P 21/005 435/69.1 |
| 2011/0206641 | A1 * | 8/2011 | Berger | A23L 33/135 424/93.4 |

FOREIGN PATENT DOCUMENTS

WO WO-2015082655 A1 * 6/2015

* cited by examiner

*Primary Examiner* — Janet L Epps-Smith
(74) *Attorney, Agent, or Firm* — WCF IP

(57) ABSTRACT

The present invention relates to pharmaceutical and food compositions for inducing satiation and prolonging satiety in subjects in need thereof. In particular, the present invention relates to a method of inducing satiation in a subject in need thereof comprising administering to the subject an effective amount of a ClpB protein or an effective amount of a bacterium that expresses the ClpB protein.

15 Claims, 1 Drawing Sheet

Specification includes a Sequence Listing.

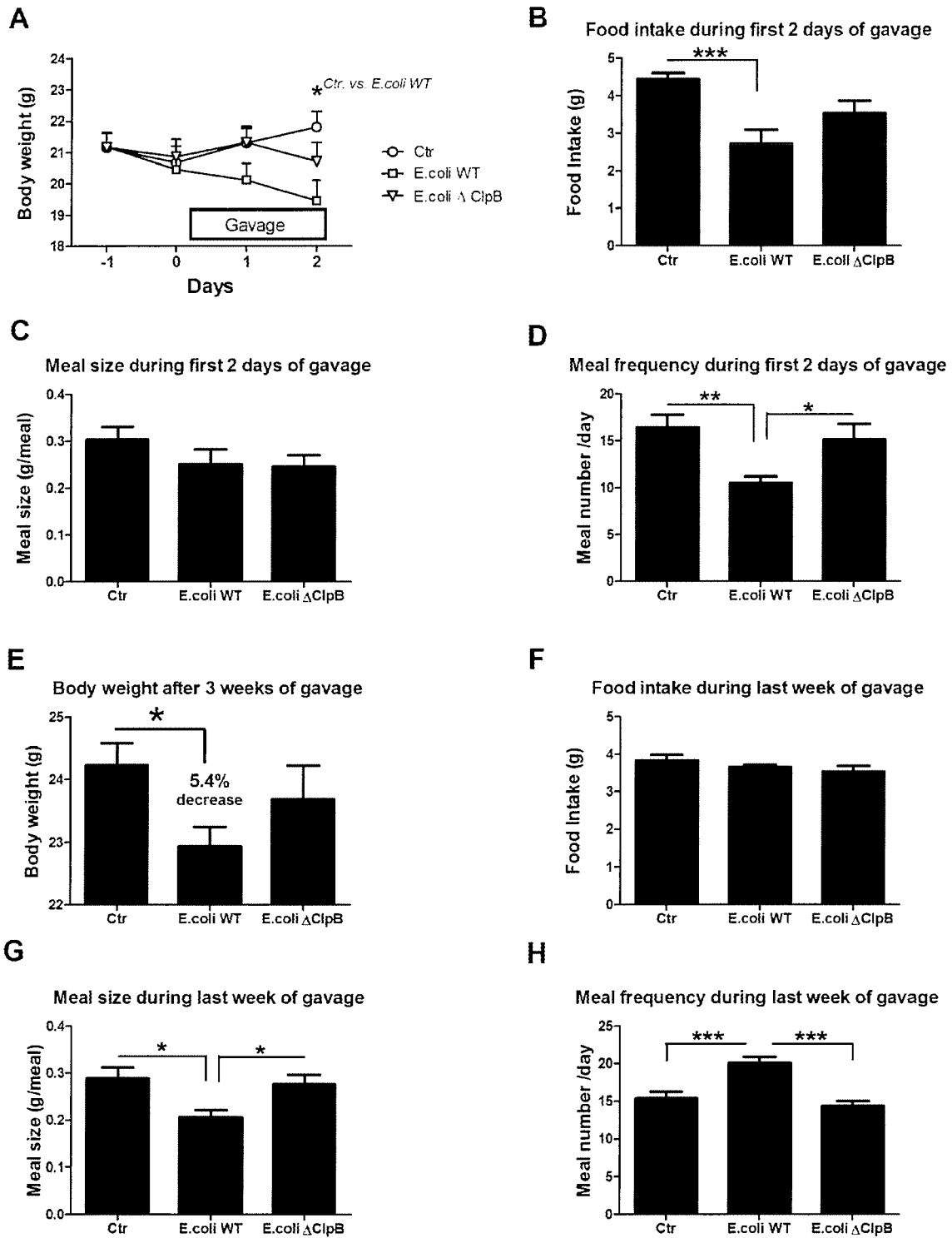

PHARMACEUTICAL AND FOOD COMPOSITIONS FOR INDUCING SATIATION AND PROLONGING SATIETY IN SUBJECTS IN NEED THEREOF

FIELD OF THE INVENTION

The present invention relates to pharmaceutical and food compositions for inducing satiation and prolonging satiety in subjects in need thereof.

BACKGROUND OF THE INVENTION

The composition of gut microbiota has been associated with host metabolic phenotypes (Ley et al., 2006) and transfer of 'obese' microbiota can induce adiposity (Turnbaugh et al., 2006) and hyperphagia (Vijay-Kumar et al., 2010), suggesting that gut microbiota may influence host feeding behavior. Although the mechanisms underlying effects of gut bacteria on host appetite are unknown, it is likely that they may use host molecular pathways controlling food intake.

The current model of food intake control implicates gut-derived hunger and satiety hormones signaling to several brain circuitries regulating homeostatic and hedonic aspects of feeding (Berthoud, 2011; Inui, 1999; Murphy and Bloom, 2006). Prominent amongst these are the anorexigenic and orexigenic pathways originating from the hypothalamic arcuate nucleus (ARC) that include the proopiomelanocortin (POMC) and neuropeptide Y (NPY)/agouti-related protein (AgRP) neurons, respectively, relayed in the paraventricular nucleus (PVN) (Atasoy et al., 2012; Cowley et al., 1999; Garfield et al., 2015; Shi et al., 2013). The ARC and PVN pathways converge in the lateral parabrachial nucleus which sends anorexigenic projections to the central amygdala (CeA), expressing calcitonin gene-related peptide (CGRP) (Carter et al., 2013; Garfield et al., 2015).

Putative mechanisms of gut microbiota effect on host control of appetite may involve its energy harvesting activities (Turnbaugh et al., 2006) and production of neuroactive transmitters and metabolites (Dinan et al., 2015; Forsythe and Kunze, 2013; Sharon et al., 2014). The inventors evidenced an implication of bacterial proteins which act directly on appetite-controlling pathways locally in the gut or systemically. In fact, several bacterial proteins have been shown to display sequence homology with peptide hormones regulating appetite (Fetissov et al., 2008), and recently ClpB protein produced by gut commensal *Escherichia coli* (*E. coli*) was identified as an antigen-mimetic of α-melanocyte-stimulating hormone (α-MSH) (Tennoune et al., 2014). α-MSH is a POMC-derived neuropeptide playing a key role in signaling satiation by activation of the melanocortin receptors 4 (MC4R) (Cone, 2005). Although MC4R-mediated α-MSH anorexigenic effects have been mainly ascribed to its central sites of actions (Mul et al., 2013), a recent study showed that activation of the MC4R in the gut enteroendocrine cells stimulates release of satiety hormones glucagon-like peptide-1 (GLP-1) and peptide YY (PYY) (Panaro et al., 2014). Thus gut bacteria-derived α-MSH-like molecules can directly act on enteroendocrine cells synthetizing satiety hormones.

SUMMARY OF THE INVENTION

The present invention relates to pharmaceutical and food compositions for inducing satiation and prolonging satiety in subjects in need thereof. In particular, the present invention is defined by the claims.

DETAILED DESCRIPTION OF THE INVENTION

The inventors have demonstrated that the ClpB protein or a bacterium that expresses the ClpB protein is capable of inducing satiation, prolonging satiety, reducing food intake, controlling weight gain, and/or stimulating weight loss in a subject in need thereof.

Accordingly, one aspect of the present invention relates to a method of inducing satiation in a subject in need thereof comprising administering to the subject an effective amount of a ClpB protein or an effective amount of a bacterium that expresses the ClpB protein.

One further aspect of the present invention relates to a method of prolonging satiety in a subject in need thereof comprising administering to the subject an effective amount of a ClpB protein or an effective amount of a bacterium that expresses the ClpB protein.

Accordingly, one aspect of the present invention relates to a method of reducing meal size in a subject in need thereof comprising administering to the subject an effective amount of a ClpB protein or an effective amount of a bacterium that expresses the ClpB protein.

One further aspect of the present invention relates to a method of reducing food intake in a subject in need thereof comprising administering to the subject an effective amount of the ClpB protein or an effective amount of a bacterium that expresses the ClpB protein.

One further aspect of the present invention also relates to a method of controlling weight gain in a subject in need thereof comprising administering to the subject an effective amount of a ClpB protein or an effective amount of a bacterium that expresses the ClpB protein.

One further aspect of the present invention also relates to a method of stimulating weight loss in a subject in need thereof comprising administering to the subject an effective amount of a ClpB protein or an effective amount of a bacterium that expresses the ClpB protein.

The methods of the present invention are intended for humans, pets or livestock, while pets or livestock may be selected from the group consisting of dogs, cats, guinea pigs, rabbits, pigs, cattle, sheep, goats, horses and/or poultry. In some embodiments, the subject is a male or female subject.

In some embodiments, the subject is not obese. In some embodiments, the subject is obese. "Obesity" refers herein to a medical condition wherein the subject preferably has a BMI of >30. The "BMI" or "body mass index" is defined as the subject's body mass divided by the square of his height. The formulae universally used in medicine produce a unit of measure of kg/m2. Typically, the non-obese subject has a normal body weight. "Normal" and "uncomplicated overweight" refers herein to body weight resulting in a BMI of between 18.5 and 30.

As used herein, the term "satiety" is meant to refer to an essentially homeostatic state wherein an individual feels that their cravings are satisfied or minimized. Many physiological factors are believed to bear on an individual's satiety. For instance, gustation, or taste, olfaction, or smell, as well as a feeling of fullness of the stomach may all contribute to whether an individual feels "satiated." More in particular, "satiety" is the state in which further eating is inhibited and determines the time between meals and the amount of food consumed at the next meal. An "enhanced feeling of satiety" or the like, this has the meaning of the feeling of satiety being more pronounced and/or more prolonged compared to a control situation. The term "satiation", as used herein refers to the state which terminates eating within a meal, typically occurring/observed within a period (e.g. 20-30 min) after the start of consuming the meal. Thus, whenever reference is made in this document to "inducing satiation" or the like, this has the meaning of arousing the tendency of a subject to stop consuming food during a meal. The effect on satiation can be determined by scoring the time point of meal termination. A satiation effect is seen if the amount of consumed calories at meal termination is significantly less than in the controls, such as for example at least 1%, 2%, 3%, 4%, 5%, 10% 20%, or more. Over a longer time period (such as 1, 2, 3, 4, 5 weeks or more), one can also score the body weight reduction or the body weight change compared to a control diet. Body weight of a subject being administered regular amounts of the test compositions (e.g. once daily, twice daily, or more) is preferably significantly controlled (reduced or less increased) compared to the control subjects. As used herein, the "control subject" refers to the subjects who were not administered with the probiotic bacterial strain of the present invention.

As used herein the term "ClpB" has its general meaning in the art and is also known as heat shock protein F84.1 which is a member of the Hsp100/ClpB family of hexameric AAA+-ATPases. ClpB has been described as an essential factor for acquired thermotolerance and for the virulence and infectivity of several Gram-negative and Gram-positive pathogenic bacteria, such as *Staphylococcus aureus, Francisella turalensis, Listeria monocylogenes, Yersinia enterocolitica*, and *Salmonella thyphimurium*. In *E. coli* K12 the chaperone protein ClpB also known as heat shock protein F84.1 or htpM and is a protein of 857 amino acids. Typically, the chaperone protein ClpB comprises or consists of the amino acid sequence of the chaperone protein ClpB from *E. Coli* K12 with SEQ ID NO: 1 (NCBI Reference Number: NP_417083.1, as available on Nov. 6, 2013 and/or UniProtKB/Swiss-Prot Number: P63284, as available on Nov. 6, 2013). Typically, the amino acid sequence of chaperone protein ClpB comprises or consists of an amino acid sequence 96 to 100% identical to the amino acid sequence of SEQ ID NO: 1. Preferably, the amino acid sequence of ClpB is 96, 97, 98, 99 or 100% identical to the amino acid sequence 540-550 (ARWTGIPVSR) of SEQ ID NO: 1. In the context of the present application, the percentage of identity is calculated using a global alignment (i.e. the two sequences are compared over their entire length). Methods for comparing the identity of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is, for example, available on the ebi.ac.uk world wide web site. The percentage of identity in accordance with the invention is preferably calculated using the EMBOSS: needle (global) program with a "Gap Open" parameter equal to 10.0, a "Gap Extend" parameter equal to 0.5, and a Blosum62 matrix. According to the invention the ClpB protein mimic the alpha-MSH protein for inducing satiation. Thus, in some embodiments, the ClpB protein of the present invention is recognized by an anti-alpha-MSH antibody. Typically, the antibody is a monoclonal antibody. In some embodiments, the antibody is a polyclonal antibody such as polyclonal rabbit anti-α-MSH IgG (1:1000, Peninsula Laboratories, San Carlos, Calif., USA). The amino acid sequence of α-MSH preferably comprises or consists of the amino acid sequence SYSMEHFRWGKPV (SEQ ID NO: 2) (Gen Pept Sequence ID, PRF: 223274, as available on Dec. 2, 2013).

```
                                            SEQ ID NO: 1
MRLDRLTNKF QLALADAQSL ALGHDNQFIE PLHLMSALLN

QEGGSVSPLL TSAGINAGQL RTDINQALNR LPQVEGTGGD

VQPSQDLVRV LNLCDKLAQK RGDNFISSEL FVLAALESRG

TLADILKAAG ATTANITQAI EQMRGGESVN DQGAEDQRQA

LKKYTIDLTE RAEQGKLDPV IGRDEEIRRT IQVLQRRTKN

NPVLIGEPGV GKTAIVEGLA QRIINGEVPE GLKGRRVLAL

DMGALVAGAK YRGEFEERLK GVLNDLAKQE GNVILFIDEL

HTMVGAGKAD GAMDAGNMLK PALARGELHC VGATTLDEYR

QYIEKDAALE RRFQKVFVAE PSVEDTIAIL RGLKERYELH

HHVQITDPAI VAAATLSHRY IADRQLPDKA IDLIDEAASS

IRMQIDSKPE ELDRLDRRII QLKLEQQALM KESDEASKKR

LDMLNEELSD KERQYSELEE EWKAEKASLS GTQTIKAELE

QAKIAIEQAR RVGDLARMSE LQYGKIPELE KQLEAATQLE

GKTMRLLRNK VTDAEIAEVL ARWTGIPVSR MMESEREKLL

RMEQELHHRV IGQNEAVDAV SNAIRRSRAG LADPNRPIGS

FLFLGPTGVG KTELCKALAN FMFDSDEAMV RIDMSEFMEK

HSVSRLVGAP PGYVGYEEGG YLTEAVRRRP YSVILLDEVE

KAHPDVFNIL LQVLDDGRLT DGQGRTVDFR NTVVIMTSNL

GSDLIQERFG ELDYAHMKEL VLGVVSHNFR PEFINRIDEV

VVFHPLGEQH IASIAQIQLK RLYKRLEERG YEIHISDEAL

KLLSENGYDP VYGARFLKRA IQQQIENPLA QQILSGELVP

GKVIRLEVNE DRIVAVQ
```

In some embodiments, the ClpB protein is administered to the subject in the form of a pharmaceutical composition. In some embodiments, the ClpB protein is combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The active ingredient can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

As used herein the expression "bacterium that expresses the ClpB" refers to a bacterium expressing or over-expressing the chaperone protein ClpB as defined above or a polypeptide comprising or consisting of an amino acid sequence 96 to 100% identical to the amino acid sequence of SEQ ID NO: 1, more preferably 96, 97, 98, 99 or 100% a identical to the amino acid sequence of SEQ ID NO: 1.

In some embodiments, the bacterium that expresses the ClpB protein is a probiotic bacterial strain.

As used herein the term "probiotic" is meant to designate live microorganisms which, they are integrated in a sufficient amount, exert a positive effect on health, comfort and wellness beyond traditional nutritional effects. Probiotic microorganisms have been defined as "Live microorganisms which when administered in adequate amounts confer a health benefit on the host" (FAO/WHO 2001). As used herein the expression "probiotic bacterial strain" denotes a bacterial strain that has a beneficial effect on the health and well-being of the host.

In some embodiments, the probiotic bacterial strain of the present invention is a viable probiotic bacterial strain. The expression "viable probiotic bacterial strain" means a microorganism which is metabolically active and that is able to colonize the gastro-intestinal tract of the subject.

In some embodiments, the probiotic bacterial strain of the present invention is a non-viable probiotic bacterial strain consisting of a mixture of bacterial fragments. In some embodiments, the mixture of bacterial fragments of the present invention consists of proteins from the bacterial strain.

In some embodiments, the probiotic bacterial stain of the present invention is selected from food grade bacteria "Food grade bacteria" means bacteria that are used and generally regarded as safe for use in food.

The bacterial strain may be a naturally occurring bacterial strain or it may be a genetically engineered bacterial strain.

In some embodiments, the probiotic bacterial strain of the present invention is a bacterium which constitutively expressed the ClpB protein.

In some embodiments, the ClpB protein is overexpressed in the bacterium. Generally a protein expression is "upregulated" or a protein is "over-expressed" when it is expressed or produced in an amount or yield that is higher than a given base-line yield that occurs in nature at standard conditions. Over-expression of a protein can be achieved, for example, by altering any one or more of: (a) the growth or living conditions of the host cells; (b) the polynucleotide encoding the protein; (c) the promoter used to control expression of the polynucleotide and its copy number in the cell; and (d) the host cells themselves.

In some embodiments, the bacterium was subjected to stress conditions so that the expression of the ClpB protein is up regulated in the bacterium. Stress may be selected from the group consisting of an exposure to heat, temperature changes, mechanical stress, or long term storage, low moisture storage and/or freeze drying or spray drying.

In some embodiments, the bacterium was subjected to nutrient supply for at least 5, 6, 7, 8, 9, 10, 11, 12, 13, 14, 15, 16, 17, 18, 19, or 20 times. Typically the nutrients are supplied by the means of a culture medium that is convenient for the growth of the bacterium, e.g. Muller-Hinton as described in the EXAMPLE. In some embodiments, the bacterium is isolated at the stage of the stationary phase that follows said repeated nutrient supply, since during this phase the concentration of the ClpB protein is maximal.

In some embodiments, the bacterium comprises at least one point mutation so that the expression of the ClpB protein is up regulated. The term "point mutation" as used herein means a nucleic acid substitution and/or deletion. Alternatively or simultaneously, the at least one mutation is located within the regulatory DNA sequences of the ClpB gene, e.g., in the transcriptional and translational control sequences, it is preferred that this mutation modulates the expression of the protein. Mutations within the regulatory DNA sequences may serve to upregulate the expression of the protein.

In some embodiments, the probiotic bacterial strain of the present invention is a bacterium which has been genetically engineered for expressing the ClpB protein. Typically, the bacterial strain was transformed with a nucleic acid encoding for the ClpB protein. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". The nucleic acid may remain extra-chromosomal upon transformation of a parental microorganism or may be adapted for intergration into the genome of the microorganism. Accordingly, the nucleic acid may include additional nucleotide sequences adapted to assist integration (for example, a region which allows for homologous recombination and targeted integration into the host genome) or stable expression and replication of an extrachromosomal construct (for example, origin of replication, promoter and other regulatory sequences). In some embodiments, the nucleic acid nucleic acid construct or vector. In some embodiments, the nucleic acid construct or vector is an expression construct or vector, however other constructs and vectors, such as those used for cloning are encompassed by the invention. In some embodiments, the expression construct or vector is a plasmid. Typically the expression construct/vector further comprises a promoter, as herein before described. In some embodiments, the promoter allows for constitutive expression of the genes under its control. However, inducible promoters may also be employed. It will be appreciated that an expression construct/vector of the present invention may contain any number of regulatory elements in addition to the promoter as well as additional genes suitable for expression of the ClpB protein if desired. Methods for transforming bacterial cell with extracellular nucleic acids are well known in the art.

In some embodiments, the probiotic bacterial strain is a gram negative strain.

In some embodiments, the probiotic bacterial strain is a member of the family of Enterobacteriaceae.

In some embodiments, the probiotic bacterial strain is an *E. coli* strain. In some embodiments probiotic *E. coli* strains for use according to the teachings of present invention include non-pathogenic *E. Coli* strains which exert probiotic activity. Example of probiotic *E. Coli* strain is the probiotic *Escherichia coli* strain BU-230-98, ATCC Deposit No. 202226 (DSM 12799), which is an isolate of the known, commercially available, probiotic *Escherichia coli* strain M-17. Example of a non-pathogenic is *E. coli* Nissle 1917. An example of *E. coli* strain which was not known as probiotic is the laboratory *E. coli* strain K12.

Typically, the probiotic bacterial strain of the present invention is produced with any appropriate culture medium well known in the art. Various fermentation media are suitable according to the invention, such as (but not limited to) e.g. firstly an industrial medium, in which the strain(s) is/are grown, and that is used as is or after concentration (e.g. drying) or after addition to another food base or product. Alternatively, bacterial cells, or bacterial cells with medium (e.g. the fermentation broth), or fractions of such cell comprising medium (i.e. medium with said bacterial strain/s) may be used. The cells or the cell comprising medium comprise live or viable bacterial cells and/or dead or non-viable bacterial cells of the strain(s). The medium may thus be treated by, but not limited to, heating or sonication. Also lyophilized, or frozen, bacteria and/or cell-free media (which may be concentrated) are encompassed in the methods for preparing the probiotic bacterial strain of the present invention.

Typically, the probiotic bacterial strain of the present invention is administered to the subject by ingestion (i.e. oral route).

In some embodiments, the probiotic bacterial strain of the present invention is encapsulated in order to be protected against the stomach. Accordingly, in some embodiments the probiotic bacterial strain of the present invention is formulated in compositions in an encapsulated form so as significantly to improve their survival time. In such a case, the presence of a capsule may in particular delay or prevent the degradation of the microorganism in the gastrointestinal tract. It will be appreciated that the compositions of the present embodiments can be encapsulated into an enterically-coated, time-released capsule or tablet. The enteric coating allows the capsule/tablet to remain intact (i.e., undissolved) as it passes through the gastrointestinal tract, until such time as it reaches the small intestine. Methods of encapsulating live bacterial cells are well known in the art (see, e.g., U.S. patents to General Mills Inc. such as U.S. Pat. No. 6,723,358). For example, micro-encapsulation with alginate and Hi-Maize™ starch followed by freeze-drying has been proved successful in prolonging shelf-life of bacterial cells in dairy products [see, e.g., Kailasapathy et al. Curr Issues Intest Microbiol. 2002 September; 3(2):39-48]. Alternatively encapsulation can be done with glucomannane fibers such as those extracted from *Amorphophallus konjac*. Alternatively, entrapment of viable probiotic in sesame oil emulsions may also be used [see, e.g., Hou et al. J. Dairy Sci. 86:424-428]. In some embodiments, agents for enteric coatings are preferably methacrylic acid-alkyl acrylate copolymers, such as Eudragit® polymers. Poly(meth)acrylates have proven particularly suitable as coating materials. EUDRAGIT® is the trade name for copolymers derived from esters of acrylic and methacrylic acid, whose properties are determined by functional groups. The individual EUDRAGIT® grades differ in their proportion of neutral, alkaline or acid groups and thus in terms of physicochemical properties. The skillful use and combination of different EUDRAGIT® polymers offers ideal solutions for controlled drug release in various pharmaceutical and technical applications. EUDRAGIT® provides functional films for sustained-release tablet and pellet coatings. The polymers are described in international pharmacopeias such as Ph. Eur., USP/NF, DMF and JPE. EUDRAGIT® polymers can provide the following possibilities for controlled drug release: gastrointestinal tract targeting (gastroresistance, release in the colon), protective coatings (taste and odor masking, protection against moisture) and delayed drug release (sustained-release formulations). EUDRAGIT® polymers are available in a wide range of different concentrations and physical forms, including aqueous solutions, aqueous dispersion, organic solutions, and solid substances. The pharmaceutical properties of EUDRAGIT® polymers are determined by the chemical properties of their functional groups. A distinction is made between:

poly(meth)acrylates, soluble in digestive fluids (by salt formation) EUDRAGIT® L (Methacrylic acid copolymer), S (Methacrylic acid copolymer), FS and E (basic butylated methacrylate copolymer) polymers with acidic or alkaline groups enable pH-dependent release of the active ingredient. Applications: from simple taste masking via resistance solely to gastric fluid, to controlled drug release in all sections of the intestine.

poly(meth)acrylates, insoluble in digestive fluids: EUDRAGIT® RL and RS (ammonio methacrylate copolymers) polymers with alkaline and EUDRAGIT® NE polymers with neutral groups enable controlled time release of the active by pH-independent swelling. Enteric EUDRAGIT® coatings provide protection against drug release in the stomach and enable controlled release in the intestine. The dominant criterion for release is the pH-dependent dissolution of the coating, which takes place in a certain section of the intestine (pH 5 to over 7) rather than in the stomach (pH 1-5). For these applications, anionic EUDRAGIT® grades containing carboxyl groups can be mixed with each other. This makes it possible to finely adjust the dissolution pH, and thus to define the drug release site in the intestine. EUDRAGIT® L and S grades are suitable for enteric coatings. EUDRAGIT® FS 30 D (aqueous dispersion of an anionic copolymer based on methyl acrylate, methyl methacrylate and methacrylic acid) is specifically used for controlled release in the colon.

Typically, the probiotic bacterial strain of the present invention is administered to the subject in the form of a food composition. Accordingly one further aspect of the present invention relates to a food composition comprising an amount of the probiotic bacterial strain of the present invention.

In some embodiments, the food composition that comprises the probiotic bacterial strain of the present invention is selected from complete food compositions, food supplements, nutraceutical compositions, and the like. The composition of the present invention may be used as a food ingredient and/or feed ingredient.

The food ingredient may be in the form of a solution or as a solid-depending on the use and/or the mode of application and/or the mode of administration.

The probiotic bacterial strain of the present invention is typically added at any time during the production process of the composition, e.g. they may be added to a food base at the beginning of the production process or they may be added to the final food product.

"Food" refers to liquid (i.e. drink), solid or semi-solid dietetic compositions, especially total food compositions (food-replacement), which do not require additional nutrient intake or food supplement compositions. Food supplement compositions do not completely replace nutrient intake by other means. Food and food supplement compositions are for example fermented dairy products or dairy-based products, which are preferably administered or ingested orally one or more times daily. Fermented dairy products can be made directly using the bacteria according to the invention in the production process, e.g. by addition to the food base, using methods known per se. In such methods, the strain(s) of the invention may be used in addition to the micro-organism usually used, and/or may replace one or more or part of the micro-organism usually used. For example, in the preparation of fermented dairy products such as yoghurt or yoghurt-based drinks, a bacterium of the invention may be added to or used as part of a starter culture or may be suitably added during such a fermentation. Optionally the bacteria may be inactivated or killed later in the production process. Fermented dairy products include milk-based products, such as (but not limited to) deserts, yoghurt, yoghurt drinks, quark, kefir, fermented milk-based drinks, buttermilk, cheeses, dressings, low fat spreads, fresh cheese, soy-based drinks, ice cream, etc. Alternatively, food and/or food supplement compositions may be non-dairy or dairy non fermented products (e.g. strains or cell-free medium in non fermented milk or in another food medium). In some embodiments, the probiotic bacterial strain of the present invention is encapsulated and dispersed in a food (e.g. in milk) or non food medium. Non-fermented dairy products may include ice cream, nutritional bars and dressings, and the like. Non-dairy products may include powdered beverages and nutritional bars, and the like. The products may be made using known methods, such as adding an effective amount of the strain(s) and/or cell-free culture medium to a food base, such as skimmed milk or milk or a milk-based composition and fermentation as known. Other food bases to which the (compositions comprising the) bacterial cells and/or cell-free culture medium may be added are meat, meat replacers or plant bases.

The composition that comprises the probiotic bacterial strain of the present invention may be solid, semi-solid or liquid. It may be in the form of a food product or food supplement, e.g. in the form of tablets, gels, powders, capsules, drinks, bars, etc. For example the composition may be in the form of a powder packed in a sachet which can be dissolved in water, fruit juice, milk or another beverage.

As used herein the term "food ingredient" or "feed ingredient" includes a formulation which is or can be added to functional foods or foodstuffs as a nutritional supplement.

By "nutritional food" or "nutraceutical" or "functional" food, is meant a foodstuff which contains ingredients having beneficial effects for health or capable of improving physiological functions.

By "food supplement", is meant a foodstuff having the purpose of completing normal food diet. A food supplement is a concentrated source of nutrients or other substances having a nutritional or physiological effect, when they are taken alone or as a combination in small amounts.

According to the invention, "functional food" summarizes foodstuff and corresponding products lately developed to which importance is attributed not only due to them being valuable as to nutrition and taste but due to particular ingredient substances. According to the invention, the middle- or long-term maintenance and promotion of health are of importance. In this context, non-therapeutic uses are preferred. The terms "nutriceuticals", "foodsceuticals" and "designer foods", which also represent embodiments of the invention, are used as synonyms, partly, however, also in a differentiated way. The preventive aspect and the promotion of health as well as the food character of the products are, however, best made clear by the term functional food. In many cases, these relate to products accumulated by assortment and selection (as is also the case in the present invention), purification, concentration, increasingly also by addition. Isolated effective substances, in particular in form of tablets or pills, are not included. Although there is no legal definition of a functional food, most of the parties with an interest in this area agree that they are foods marketed as having specific health effects beyond basic nutritional effects. Accordingly, functional foods are ordinary foods that have components or ingredients (such as those described herein) incorporated into them that impart to the food a specific functional e.g. medical or physiological benefit other than a purely nutritional effect.

In some embodiments, the drink is a functional drink or a therapeutic drink, a thirst-quencher or an ordinary drink. By way of example, the composition of the present invention can be used as an ingredient to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

In some embodiments, the composition that comprises the probiotic bacterial strain of the present invention is used with yoghurt production, such as fermented yoghurt drink, yoghurt, drinking yoghurt, cheese, fermented cream, milk based desserts and others. Suitably, the composition can be further used as an ingredient in one or more of cheese applications, meat applications, or applications comprising protective cultures.

In some embodiments, the food composition that comprises the probiotic bacterial strain of the present invention is suitable for preparing meal replacement product. As used herein, the term "meal replacement product" as used herein, unless otherwise specified, includes any nutritional product containing protein, carbohydrate, lipid, vitamins and minerals, the combination of which is then suitable as a sole or primary nutrition source for a meal. Typically, the meal replacement product comprises at least one carbohydrate source, at least one lipid source and/or at least one protein source. As protein source any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. The proteins may be intact or hydrolysed or a mixture of intact and hydrolysed proteins. It may be desirable to supply partially hydrolysed proteins (degree of hydrolysis between 2 and 20%), for example for animals believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source. If the composition includes a fat source, the fat source preferably provides 5% to 40% of the energy of the composition; for example 20% to 30% of the energy. A suitable fat profile may be obtained using a blend of canola oil, corn oil and high-oleic acid sunflower oil. The source of carbohydrates preferably provides 40% a to 80% of the energy of the composition. Any suitable carbohydrate may be used, for example sucrose, lactose, glucose, fructose, corn syrup solids, maltodextrins, and mixtures thereof. Typically, substituting one daily meal by an energy restricted diet with a meal replacement contributes to the maintenance of weight after weight loss.

The food composition that comprises the probiotic bacterial strain of the present invention typically comprises carriers or vehicles. "Carriers" or "vehicles" mean materials suitable for administration and include any such material known in the art such as, for example, any liquid, gel, solvent, liquid diluent, solubilizer, or the like, which is non-toxic and which does not interact with any components of the composition in a deleterious manner. Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

In some embodiments, the food composition that comprises the probiotic bacterial strain of the present invention comprises an amount of dietary fibres. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyl-lactose and oligosaccharides derived from animal milks. In some embodiments, the dietary fiber is selected among mannans. Mannans (such as glucomannans and galactomannans), such as guar gum, locust bean gum, konjac, and xanthan gum, are present in some plant cell walls. The glucomannans are generally comprised of (1-4)-β-linked glucose and mannose units, while the galactomannans are generally comprised of a (1-4)-β-mannan backbone substituted with single units of (1-6)-α-galactose. Many endospermic legumes, such as guar and locust bean, contain galactomannans in the endosperm during seed development. Glucomannans have also been found as a minor component of cereal grains.

In some embodiments, the food composition that comprises the probiotic bacterial strain of the present invention contains minerals and micronutrients such as trace elements and vitamins in accordance with the recommendations of Government bodies such as the USRDA. For example, the composition may contain per daily dose one or more of the following micronutrients in the ranges given: 300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

In some embodiments, the composition that comprises the probiotic bacterial strain of the present invention contains emulsifiers. Examples of food grade emulsifiers typically include diacetyl tartaric acid esters of mono- and di-glycerides, lecithin and mono- and di-glycerides. Similarly suitable salts and stabilisers may be included.

In some embodiments, the food composition that comprises the probiotic bacterial strain of the present invention contains at least one prebiotic. "Prebiotic" means food substances intended to promote the growth of the probiotic bacterial strain of the present invention in the intestines. The prebiotic may be selected from the group consisting of oligosaccharides and optionally contains fructose, galactose, mannose, soy and/or inulin; and/or dietary fibers.

In some embodiments, the composition that comprises the probiotic bacterial strain of the present invention contains protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

In some embodiments, the administration of the ClpB protein (or the probiotic bacterial strain that express the protein) is repeated, for example, 2 to 3 times a day, for one day or more and generally for a sustained period of at least 4 days, or even 4 to 15 weeks, with, where appropriate, one or more periods of interruption. In some embodiments, the ClpB protein is administered simultaneously or sequentially one meal of the subject. In some embodiments, the ClpB protein is administered prior to the meal of the subject.

As used herein, the term "effective amount" refers to a quantity sufficient of ClpB protein to achieve the beneficial effect (e.g. stimulating satiety, prolonging satiation, reducing food intake, controlling weight gain, and/or stimulating weight loss). In the context of the present invention, the amount of a ClpB protein administered to the subject will depend on the characteristics of the individual, such as general health, age, sex, body weight . . . . The skilled artisan will be able to determine appropriate dosages depending on these and other factors. For example, when the ClpB protein is administered to the subject in the form a protbiotic, the strain of the present invention shall be able to generate a colony is sufficient to generate a beneficial effect on the subject. If the probiotic bacterial strain is administered in the form of a food product, it typically may comprise between $10^3$ and $10^{12}$ cfu of at the probiotic bacterial strain of the present invention per g of the dry weight of the food composition.

The invention will be further illustrated by the following FIGURES and examples. However, these examples and FIGURES should not be interpreted in any way as limiting the scope of the present invention.

FIGURES

FIG. 1: Effects of daily intragastric delivery of *E. coli* K12 wild type (WT) or *E. coli* deleted for ClpB gene (ΔClpB) in normal C57Bl6 adult mice on body weight, 24 h food intake and meal pattern analyzed at the beginning and the end of 3 weeks of gavage. Control mice (Ctr) did not receive any gavage. Meal pattern was measured as meal size, corresponding to an average amount of food eaten during a single meal, and as meal frequency, corresponding to a number of meals per 24 h separated by at least 5 min. Decreased meal size reflects faster satiation and decreased meal frequency reflects longer satiety. A. Two-way repeated measurements ANOVA, Bonferroni post-test *$p<0.05$. B,D,G,H, ANOVA, Tukey's post-tests, *$p<0.05$, $p<0.01$, *$p<0.001$. E. Student's t-test, *$p<0.05$.

EXAMPLE 1

Material & Methods

In Vitro *E. coli* Growth after Regular Nutrient Supply

The *E. coli* K12 bacteria were cultured at 37° C. in 40 mL of MH medium (Becton, Dickinson, Md.) containing 3000 beef infusion, 1.7500 casein hydrolysate and 0.15% starch with pH 7.3 at 25° C. in 50 ml Falcon vials. For modeling two scheduled daily meals in humans, bacteria received new MH medium every 12 h during 5 consecutive days. Bacterial growth was measured as an OD at λ=600 nm by a spectrophotometer every 2 h after the $1^{st}$ provision of MH medium, every 1 h after the $3^{rd}$ and every 10 min after the $5^{th}$ provisions. At the end of each 12 h cycle, bacteria were centrifuged for 5 min at 6,000 rpm at room temperature (RT). The supernatants were discarded and replaced by an equivalent volume (~40 ml) of a new MH medium. After the last supplementation of MH medium, bacteria were sampled for protein extraction in the exponential phase and in the following stationary phase.

Protein Extraction

*E. coli* K12 bacteria were centrifuged at 4° C. for 30 min at 4,000 g. Bacterial residues were dissolved in 2 ml of trishydroxymethylaminomethane (TRIS) buffer (pH 7.4) and homogenized by sonication for 3 min at RT. To separate proteins from the undissolved cell fragments, the bacterial homogenate was centrifuged at 4° C. for 30 min at 10,000 g. The supernatant was recovered and then ultracentrifuged at 4° C. for 45 min at 60,000 g to further separate proteins into cytoplasmic (supernatant) and membrane (residues) fractions. Membrane proteins were dissolved in TRIS buffer (pH 7.4). Protein concentrations were measured using 2-D Quant Kit (GE Healthcare, Piscataway, N.J.).

Two-Dimensional Polyacrylamide Gel Electrophoresis

For 2D-PAGE, 300 µg of *E. coli* protein extract were used to rehydrate immobilized pH gradient (IPG) strips (pH 4-7; 18 cm: BIO-RAD, Hercules, Calif.). Proteins were then resolved in the first dimension by isoelectric focusing for a total of 85,000 V-h by using the IPGphor isoelectric focusing system (GE Healthcare). After focusing, IPG strips were incubated for 15 min in the equilibration buffer [urea 6 mol/L, 30% (vol:vol) glycerol, 2% (wt:vol) sodium dodecyl sulfate (SDS), Tris-HCl 50 mmol/L pH 8.8, and 0.250 (wt:vol) bromophenol blue containing 2% (wt:vol) dithiothreitol] and then alkylated for 15 min in the equilibration buffer containing 4% (wt:vol) iodoacetamide. IPG strips were subsequently affixed onto 10%0 polyacrylamide gradient gels (20 cm·18 cm·1 mm) for SDS-PAGE. The second dimension was performed overnight in the Ettan Daltsix vertical electrophoresis system (GE Healthcare) with 12 mA/gel at 25° C. After SDS-PAGE, the 2D gels were fixed for 2 h in 200 (vol:vol) orthophosphoric acid and in 50.0 (vol:vol) methanol at RT. Gels were then rinsed with water, and the protein spots were visualized by CBB G-250 (BIO-RAD) staining [34% (vol:vol) methanol, 17% (wt:vol) ammonium sulfate, 2% (vol:vol) orthophosphoric acid, and 0.66 g CBB G-250/L].

Analysis of Differential Protein Expression

Images of stained 2D gels were scanned by an ImageScanner II (GE Healthcare) calibrated with a grey scale marker (Kodak, Rochester, N.Y.) and digitalized with Labscan 6.0 software (GE Healthcare). Analysis of differential protein expression including spot detection, quantification, matching, and comparative analysis was performed using ImageMaster 2D Platinum 5.0 software (GE Healthcare). Each protein sample was subjected to 2D-PAGE at least 3 times (membrane proteins) and 4 times (cytoplasmic proteins) to minimize run-to-run variation, and each set of 3 (or 4) gels was compared using ImageMaster to confirm the nonappearance of statistically differential spots within the set of gels. The most representative gel (gel migration, spot definition, and spot number) of each set was used to compare E. coli proteins between exponential and stationary phases. The expression level was determined by the relative volume of each spot in the gel and expressed as % volume, calculated as spot volume/Σvolumes of all spots resolved in the gel. This normalized spot volume takes into account variations due to protein loading and staining by considering the total volume over all the spots present in the gel. Variations in abundance were calculated as the ratio of average values of % volume for a group of spots between the 2 phases. Only spots with a volume variation ratio >1.5 were considered relevant. The absence of a spot within a gel indicated that no detectable expression could be reported for a protein under the selected experimental condition. The corresponding p values were determined by Student's t-test (significance level $p<0.05$) after spot volume log-transformation.

Protein Identification by Liquid Chromatography-Electrospray Ionization MS/MS

The protein spots of interest were excised from CBB G-250-stained 2D gels using the Ettan Spot Picker (GE Healthcare), and automated in-gel digestion of proteins was performed on the Ettan Digester (GE Healthcare) as previously described (Goichon et al., 2011). Protein extracts were then resuspended in 10 μL of 500 (vol:vol) acetonitrile/0.1% (vol:vol) formic acid and then analyzed with a nano-LC1200 system coupled to a 6340 Ion Trap mass spectrometer equipped with a nanospray source and an HPLC-chip cube interface (Agilent Technologies, Courtaboeuf, France). Briefly, peptides were enriched and desalted on a 40 nL RP-C18 trap column and separated on a Zorbax (30-nm pore size, 5-μm particle size) C18 column (43 mm long×75 μm inner diameter; Agilent Technologies). A 9-min linear gradient (3%-80% acetonitrile in 0.1% formic acid) at a flow rate of 400 nL/min was used and the eluent was analyzed with an ion trap mass spectrometer.

For protein identification, MS/MS peak lists were extracted and compared with the protein databases by using the MASCOT Daemon version 2.2.2 (Matrix Science) search engine. The searches were performed with the following specific parameters: enzyme specificity, trypsin; one missed cleavage permitted; no fixed modifications, variable modifications, methionine oxidation, cysteine carbamidomethylation, serine, tyrosine and threonine phosphorylation; monoisotopic; peptide charge, 2+ and 3+; mass tolerance for precursor ions, 1.5 Da; mass tolerance for fragment ions, 0.6 Da; ESI-TRAP as instrument; taxonomy, E. coli; National Center for Biotechnology Information (NCBI) database [NCBInr 20120531 (18280215 sequences, 6265275233 residues)] (Bethesda, Md.). Protein hits were automatically validated if they satisfied one of the following criteria: identification with at least two top ranking peptides (bold and red) each with a MASCOT score of more than 54 ($p<0.01$), or at least two top ranking peptides (bold and red) each with a MASCOT score of more than 47 ($p<0.05$). To evaluate false-positive rates, all the initial database searches were performed using the "decoy" option of MASCOT. Results were considered relevant if the false-positive rate never exceeded 1%.

ATP Assay

In vitro ATP production was measured using ATP colorimetric/fluorometric assay kit according to the manufacturer's instructions (BioVision, CA). Briefly, bacterial proteins from the exponential or stationary phases were placed into a series of wells in duplicates for each concentration (1, 10 and 25 μg/mL in ATP assay buffer) and adjusted to 50 μL/well with ATP assay buffer. Then 10 μL of different nutrients solution, 15% sucrose or MH medium were added to corresponding wells and adjusted to 50 μL/well with the ATP assay buffer; 50 μL/well of ATP buffer only was added to control wells. The plate was incubated 2 h at 37° C. After the incubation, 50 μL of ATP reaction mix (containing ATP assay buffer, ATP probes, ATP converter and developer mix) were added in each wells. OD was measured at 570 nm after 30 min of incubation at RT, protected from day light.

Development and Validation of ClpB Immunoassay

Design of the ClpB detection assay was based on several criteria, such as a specific and sensitive detection in a linear concentration range. A particular condition was the ClpB detection without α-MSH cross-reactivity, which may occur due the presence of α-MSH-like epitope(s) in the ClpB molecule. For simplicity of the procedure and signal detection, we used a standard 96-well ELISA plate and an option of the OD reading by a spectrophotometer. The detailed protocols of the ClpB ELISA and Western blot (WB) are presented in separate sections.

To prevent binding of the Revelation antibody (Ab) to the Capture Ab, we produced ClpB Capture Ab and ClpB Detection Ab in different species, rabbit and mouse, respectively. For the most efficient capture of the ClpB protein from complex biological samples, we coated the ELISA plate with rabbit polyclonal Ab having multiple anti-ClpB epitopes. To avoid cross-reactivity between ClpB and α-MSH we used, as the Detection Ab, a mouse monoclonal anti-ClpB Ab that has been characterized by high sensitivity and specificity to recognize ClpB but not α-MSH preselected by ELISA screening of several Ab clones. Alkaline phosphatase-conjugated anti-mouse Revelation Ab was used as a common ELISA tool to obtain a chromogenic enzymatic reaction readable as an OD proportional to the analyte concentration. A linear change in OD resulting from the detection of 7 consecutive dilutions of a recombinant E. coli ClpB protein ranging from 2 pM to 150 pM was obtained without reaching a plateau and without saturation of the OD signal.

To validate the specificity of the developed ClpB assay, we measured ClpB concentrations in protein samples extracted from 10 different cultures of E. coli K12 WT and from a culture of ΔClpB mutant E. coli bacteria. ΔClpB mutant and the corresponding wild type (WT) strains were kindly provided by Dr. Axel Mogk (ZMBH, Heidelberg University, Germany). Furthermore, we analyzed the ClpB presence in these bacterial protein samples by WB using anti-ClpB polyclonal rabbit Ab and compared the signal intensity values between the WB bands and ClpB concentrations in ELISA. ClpB was detected in all WT E. coli cultures, with 7 cultures having ClpB concentrations higher than 1000 pM, while ClpB was not detectable in the protein sample extracted from ΔClpB E. coli. WB revealed a major band of an expected 96 KDa size in WT but not in ΔClpB E. coli. The OD intensity of these bands varied between individual samples and correlated positively with ClpB concentrations measured by ELISA in the same samples of E. coli cultures. Thus, the absence of ClpB detection in protein preparations of ΔClpB E. coli confirmed the specificity of the assays, and a good accordance between the ELISA and WB provided the cross-validation of both ClpB immunodetection techniques.

To verify that ClpB plasma assay detects ClpB derived from gut bacteria, we used the ClpB ELISA to measure ClpB in plasma of mice which had been supplemented via intragastric gavage daily for 3 weeks with WT or with ΔClpB E. coli. Plasma samples were available from our previously published study (Tennoune et al., 2014). We found that ClpB was normally present in mouse plasma including both controls and mice gavaged with a culture broth without bacteria. Importantly, ClpB plasma levels were increased in mice receiving WT E. coli but were unchanged in mice supplemented with ClpB-deficient E. coli, confirming the gut bacterial origin of plasmatic ClpB.

ClpB ELISA

Rabbit polyclonal anti-E. coli ClpB antibodies (customly produced by Delphi Genetics, Gosselies, Belgium), were coated onto 96-well Maxisorp plates (Nunc, Rochester, N.Y.) using 100 µl and a concentration of 2 µg/ml in 100 mM NaHCO3 buffer, pH 9.6 for 12 h at 4° C. Plates were washed (5 min×3) in phosphate-buffered saline (PBS) with 0.05°% Tween 20, pH 7.4. The recombinant E. coli ClpB protein (customly produced by Delphi Genetics), was diluted serially to 5, 10, 25, 50, 70, 100 and 150 pM in the sample buffer (PBS, sodium azide 0.02%, pH 7.4) and added to the wells in duplicates to make a standard. The analyte samples included: colonic mucosa and plasma samples from mice and rats or proteins extracted from E. coli K12 cultures. Analyte samples were added to the remaining wells in duplicates and were incubated 2 h at RT. Plates were washed (5 min×3) in PBS with 0.05% Tween 20, pH 7.4. Mouse monoclonal anti-E. coli ClpB antibodies (1:500 in sample buffer, customly produced by Delphi Genetics) were added to the wells and incubated 90 min at RT. Plates were washed (5 min×3) in PBS with 0.05% Tween 20, pH 7.4. Goat anti-mouse IgG conjugated with alkaline phosphatase (1:2000 in sample buffer) from Jackson ImmunoResearch Laboratories, Inc. (West Grove, Pa.) were added to the wells and incubated for 90 min at RT. Plates were washed (5 min×3) in PBS with 0.05% Tween 20, pH 7.4 and then 100 µl of p-nitrophenyl phosphate solution (Sigma, St. Louis, Mo.) was added as alkaline phosphatase substrate. After 40 min of incubation at RT, the reaction was stopped by adding 50 µL of 3N NaOH. The OD was determined at 405 nm using a microplate reader Metertech 960 (Metertech Inc., Taipei, Taiwan). Blank OD values resulting from the reading of plates without addition of plasma samples or ClpB protein standard dilutions were subtracted from the sample OD values.

ClpB Western Blot

Western blot was performed using proteins extracted from E. coli K12. Protein samples (10 µg) were separated on 20% acrylamide SDS gel in Tris-Glycine buffer and transferred to a nitrocellulose membrane (GE Healthcare, Orsay, France), which was blocked for at least 1 h at RT with 5% (w/v) non-fat dry milk in TBS (10 mmol/L Tris, pH 8; 150 mmol/L NaCl) plus 0.05% (w/v) Tween 20. Then, the membrane was incubated overnight at 4° C. with rabbit polyclonal anti-E. coli ClpB antibodies (1:2000, Delphi Genetics). After three washes in a blocking solution of 5%0 (w/v) non-fat dry milk in TBS/0.05% Tween 20, membranes were incubated for 1 h with peroxidase-conjugated anti-rabbit IgG (1:3000, SantaCruz Biotechnology). After three washes, the peroxidase reaction was revealed using the ECL detection kit (GE Healthcare). Protein bands were compared with the molecular weight standard (Precision Plus, BioRad) and films were scanned using ImageScanner III (GE Healthcare) and analyzed for the band pixel density using the ImageQuant TL software 7.0 (GE Healthcare).

Intestinal Administrations of E. coli Proteins in Rats

Animals

Animal care and experimentation were in accordance with guidelines established by the National Institutes of Health, USA and complied with both French and European Community regulations (Official Journal of the European Community L 358, 18 Dec. 1986). Female Sprague-Dawley rats, body weight 200-250 g (Janvier, Genest-Saint-Isle, France) were kept in holding cages (3 rats per cage) in a fully equipped animal facility under regulated environmental conditions (22±1° C., on a 12 h light-dark cycle with lights on at 7:30 a.m.) for 1 week in order to acclimatize them to the housing conditions. Standard pelleted rodent chow (RM1 diet, SDS, UK) and drinking water were available ad libitum.

EXPERIMENT #1

This experiment was designed to evaluate the relevance of our in vitro model of E. coli growth to in vivo situations of bacterial growth in the gut. Rats were anaesthetized by ketamine (75 mg/kg, Virbac, Carros, France)/xylazine (5 mg/kg, Bayer, Leverkusen, France) solution, 3:1 vol., 0.1 mL/100 g body weight I.P. After laparotomy, colon was mobilized by placing 2 ligatures: $1^{st}$ at the caecocolonic junction and the $2^{nd}$, 4 cm below. Colonic infusions and luminal content sampling were performed using a polypropylene catheter inserted into the ascending colon and fixed with the $1^{st}$ ligature. 2 ml of MH medium or water were gently infused into the colon and immediately thereafter withdrawn for the measurement of OD. After OD measurement, the whole sample of the colonic content was returned into the colon. Such sampling of the colonic content, without adding new MH medium or water, was repeated every 5 min during first 20 min and then at 30 min and 60 min. Bacterial density was measured as an OD at λ=600 nm by a spectrophotometer. Blood samples were taken from the portal vein before and 30 and 60 min after the $1^{st}$ infusion. Faecal samples were taken from the colon at the end of experiment for DNA extraction and PCR of ClpB.

Real-Time Quantitative Polymerase Chain Reaction

Quantitative PCR (qPCR) was performed to analyze bacterial density of ClpB DNA expressing bacteria using a CFX 96 q-PCR instrument (BioRad, CA). Total DNA was extracted from the rat faeces using QAMP DNA stool mini kit (QIAGEN Venlo, Netherlands). The qPCR mix included 5 µl of SYBR Green Master (QIAgen, West Sussex, UK), 0.5 µM each of forward and reverse primers, DNA from samples and water to give a total volume of 10 µl. The primers were purchased from Invitrogen (Cergy-Pontoise, France). A three-step PCR was performed for 40 cycles. The samples were denatured at 95° C. for 10 min, annealed at 60° C. for 2 min, and extended at 95° C. for 15 s.

EXPERIMENT #2

This experiment aimed to evaluate effects of *E. coli* proteins on intestinal peptides (GLP-1 and PYY) release in the systemic circulation. Rats were anaesthetized and the colon was mobilized as described above, colonic infusions of *E. coli* proteins (0.1 µg/kg of protein in 2 ml of PBS) extracted in the exponential (n=6) or in the stationary phase (n=6) were preformed once for 20 min. Blood samples were taken from the portal vein before and after 20 min of colonic infusions for assays of GLP-1, PYY and ClpB Samples of colonic mucosa were taken at the end of experiment for ClpB assay. GLP-1 and PYY assays were performed using a fluorescent enzyme immunoassay kit (Phoenix Pharmaceutical inc., CA), according to the manufacturer's instructions. The fluorescence was measured at 325 nm for excitation and 420 nm for emission using a microplate reader Chameleon (HIDEX Inc., Turku, Finland).

Administrations of *E. coli* Proteins in Rats, Food Intake and Brain c-Fos Study Animals Male Wistar rats, body weight 200-250 g (Janvier, Genest-Saint-Isle, France) were acclimatized to the housing conditions and were fed as described above. Three days before experiments, the rats were transferred to individual metabolism cages (Tecniplast, Lyon France) where they were fed ad libitum with the same RM1 diet but in powdered form (SDS). Drinking water was always available. The rats were gently handled daily for several min during the acclimation period to habituate them to manipulations. At the end of acclimation, rats were distributed into three groups to achieve similar mean body weight and were used in the Experiments 1-3. Two experiments including food restriction were performed in the same rats with 4 days interval. The $3^{rd}$ experiment in free feeding rats involved their new series.

EXPERIMENT #1

The $1^{st}$ experiment was aimed to compare effects of membrane proteins of *E. coli* extracted in exponential and stationary phases. Rats were deprived from food overnight (between 18.00 h and 10.00 h), while water was available ad libitum. On following day after food deprivation, *E. coli* proteins were injected I.P. at 10.00 h and rats immediately returned to their metabolism cages, which contained a pre-weighed amount of food. Food intake was measured at 1, 2, and 4 h. The $1^{st}$ group of rats (n=6) received 0.1 mg/kg of membrane proteins extracted from *E. coli* in exponential phase in 300 µl of PBS; the $2^{nd}$ group of rats (n=6) received 0.1 mg/kg of membrane proteins extracted from *E. coli* in stationary phase and the control group (n=6) received 300 µl of PBS.

EXPERIMENT #2

The $2^{nd}$ experiment was aimed to compare effects of cytoplasmic proteins of *E. coli* extracted in exponential and stationary phases. A similar experimental protocol was used as that for Experiment #1.

EXPERIMENT #3

This experiment was designed to evaluate effects of total *E. coli* proteins on food intake in free feeding rats. Injections of *E. coli* proteins (0.1 mg/kg of protein in 300 µl PBS, I.P.) extracted in the exponential (n=6) or in the stationary phase (n=6) or PBS only as control (n=6), were carried out at 19.30 h and the animals were returned to their metabolism cages which contained a pre-weighed amount of food. Cumulative food intake was measured after 2 h. Immediately thereafter, rats of were anaesthetized by sodium pentobarbital (0.2 mg/kg, I.P.) and perfused for the immunohistochemical study of c-fos expression in the brain.

Tissue Preparation and Immunohistochemistry

Brains were fixed by perfusion/immersion in 4%0 paraformaldehyde, frozen and cut (14 µm) on a cryostat (Leica Microsystems, Nanterre, France) and then processed for immunohistochemistry using a tyramide signal amplification (TSA) plus fluorescein kit (NEN, Boston, Mass.). For single staining, rabbit polyclonal antisera against c-fos (1:4, 000, Ab-5, Calbiochem, Merck KGaA, Darmstadt, Germany) was used. For double staining, following the TSA, a direct immunofluorescence technique was applied using either rabbit monoclonal antibodies against β-endorphin (β-end) 1:1,000 (Life Technologies, Frederick, Md.) which was revealed by anti-rabbit Cyanine-3 antibodies 1:200 (Jackson ImmunoResearch, West Grove, Pa.) or mouse monoclonal IgG against calcitonin gene-related peptide (CGRP) 1:1,000 (Santa Cruz Biotechnology, inc., TX) which was revealed by anti-mouse rhodamine red-conjugated antibodies 1:200 (Jackson ImmunoResearch). In the hypothalamic arcuate and ventromedial nuclei and in the central nucleus of amygdala, positive cells were counted at ×20 magnification from six consecutive sections. The mean number of positive cells per rat was used to calculate the group mean. Digital images were optimized for brightness and contrast in Adobe Photoshop 6.0 software (Adobe Systems, San Jose, Calif.).

Chronic Administrations of *E. coli* Proteins in Mice

Two-month-old male C57Bl6 mice (n=32) were purchased from Janvier Labs and acclimated to the animal facility for 1 week with 12 h light-dark cycle, lights on at 8:00. Then, the mice were placed individually in the BioDAQ mouse cages (Research Diets, Inc., New Brunswick, N.J.), each equipped with an automatic feeding monitor. After 3 days of acclimation to the BioDAQ cages, mice were divided into three groups (n=8), each receiving different treatments consisting of two daily I.P. injections at 9:00 and at 18:30 of either: (i) PBS, (ii) bacterial proteins extracted in exponential phase (0.1 mg/Kg of body weight), (iii) bacterial proteins extracted in stationary phase (0.1 mg/Kg of body weight). Food (SERLAB, Montataire, France) and drinking water were available ad libitum and body weight was measured daily. Feeding data were continuously monitored for one week and analyzed using the BioDAQ data viewer 2.3.07 (Research Diets). For the meal pattern analysis, the inter-meal interval was set at 300 s. The satiety ratios were calculated as time (s) of post-meal interval divided by amount of food (g) consumed in the preceding meal. After the experiment, mice were killed by decapitation; the brain was removed and the hypothalamus dissected for the neuropeptide mRNA microarray.

Hypothalamic Neuropeptide mRNA Microarray

Total RNA was extracted from the hypothalamus of mice, which received chronic administrations of *E. coli* proteins, using the NucleoSpin® RNA II kit (Macherey-Nagel, Düren, Germany) following the manufacturers' protocol. Digested RNA were reverse-transcribed at 42° C. for 60 min using the ImProm-II™ Reverse Transcription System kit (Promega, Madison, Wis.). Obtained cDNA was used in real-time PCR reaction. A panel of 9 primer pairs was designed with the Primer express software (Life Technologies, Saint-Aubin, France) and validated for efficiency and specificity. The PCR reaction, composed of 6 µl of cDNA and of 6 µl of Fast SYBR Green Master Mix (Life Technologies) containing specific reverse and forward primers at a concentration of 100 nM, was dispensed in 96-well plates with a Bravo liquid handling system (Agilent) and amplified with a QuantStudio 12K Flex (Life Technologies). The cDNA-generated signals for target genes were internally corrected with that of reference gene signals for variations in amounts of input mRNA. Gene expression level was then compared to a corresponding control sample group, and regulations were determined with the $2^{\Delta\Delta Cq}$ method.

Electrophysiological Recordings

Brain slice (250 µm) were prepared from adult POMC-eGFP mice (5-7 weeks old; Ref: C57BL/6J-Tg(Pomc-EGFP)1Low/J, The Jackson Laboratory) as previously described (Fioramonti et al., 2007). Slices were incubated at RT, in oxygenated extracellular medium containing (in mM): 118 NaCl, 3 KCl, 1 $MgCl_2$, 25 NaHCO3, 1.2 $NaH_2PO_4$, 1.5 CaCl2), 5 Hepes, 2.5 D-glucose (osmolarity adjusted to 310 mOsM with sucrose, pH 7.4) for a recovery period at least 60 min. Once in the recording chamber, slices were perfused at 2-3 ml/min with the same extracellular medium. Slices were viewed with a Nikon microscope EF600 (Nikon France, Champigny sur Marne) outfitted for fluorescence (fluorescein filter) and IR-DIC video microscopy. Viable ARC POMC neurons were visualized using a X40 water immersion objective (Nikon) with a fluorescence video camera (Nikon). Borosilicate pipettes (4-6 MΩ; 1.5 mm OD, Sutter Instruments, Novato, Calif.) were filled with filtered extracellular medium. Cell-attached recordings were made using a Multiclamp 700B amplifier, digitized using the Digidata 1440A interface and acquired at 3 kHz using pClamp 10.3 software (Axon Instruments, Molecular Devices, Sunnyvale, Calif.). Pipettes and cell capacitances were fully compensated. After a stable baseline was established, 1 nM of ClpB (Delphi Genetics) was perfused for 5-10 minutes. The POMC neurons' firing rate was measured over the last 3 min of the ClpB perfusion, 7-10 min after the perfusion and compared with the firing rate measured 3 min before the perfusion.

Statistical Analysis

Data were analyzed and the graphs were plotted using the GraphPad Prism 5.02 (GraphPad Software Inc., San Diego, Calif.). Normality was evaluated by the Kolmogorov-Smirnov test. Group differences were analyzed by the analysis of variance (ANOVA) or the non-parametric Kruskal-Wallis (K-W) test with the Tukey's or Dunn's post-tests, according to the normality results Where appropriate, individual groups were compared using the Student's t-test and Pearson's correlations or the Mann-Whitney (M-W) test according to the normality results. Effects of continuous experiments were analysed using repeated measurements (RM) ANOVA and the Bonferroni post-tests. Data shown as means±standard error of means (s.e.m), and for all test, $p<0.05$ was considered statistically significant.

Results

*E. coli* Growth after Regular Nutrient Provision

After the $1^{st}$ provision of the Müeller-Hinton (MH) nutritional medium to *E. coli* culture, three phases of bacterial growth were observed: 1) lag phase of 2 h; 2) exponential growth phase of 4 h and 3) stationary phase with the 0.35 optical density (OD) remaining stable for 6 h. After the $3^{rd}$ and $5^{th}$ MH medium supplies, only two growth phases were found: the exponential and stationary, the $1^{st}$ phase starting immediately after the nutrient provision. Each new feeding cycle was characterized by a shorter duration of the exponential growth phase: 2 h after the $3^{rd}$ and 20 min after the $5^{th}$ provision. After the $5^{th}$ nutrient provision, bacterial proteins were extracted and separated into the membrane and cytoplasmic fractions used for the proteomic analysis and in vivo experiments in fasted rats. In the new experiment, to verify if continuing regular nutrient provision may further accelerate the dynamics of bacterial growth, *E. coli* K12 were supplied with nutrients 9 times. We found that, after the $7^{th}$ and $9^{th}$ nutrient provisions, the exponential growth phase did not further change, lasting for 20 min with the same (Δ0.3) relative increase in OD, reflecting an identical bacterial growth after each supply of nutrients. According to the McFarland standards, an increase of 0.3 OD corresponds to an increment of $10^8$-$10^9$ of bacteria. After the $9^{th}$ nutrient provision, bacterial proteins were extracted in the exponential and stationary phases, showing total protein concentrations of 0.088 mg/ml and 0.15 mg/ml, respectively. The extracted proteins were tested for ClpB levels and have been used in the ATP production assay and for in vivo experiments including intracolonic infusions and systemic injections in free feeding mice and rats followed by the c-fos detection in the brain.

Proteomic Analysis

To analyze whether the protein expression profiles vary according to nutrient-induced bacterial growth phases, two-dimensional polyacrylamide gel electrophoresis (2D-PAGE) was performed separately on membrane and cytoplasmic fractions of *E. coli* K12 proteins extracted 10 min and 2.3 h after the $5^{th}$ addition of MH medium, corresponding to the exponential and stationary phases, respectively. The total number of detected protein spots was 2895 (1367 membrane and 1528 cytoplasmic).

Comparison of the 2D-PAGE of membrane proteins between the exponential and stationary phases revealed 20 differentially (by at least 1.5 fold) expressed proteins. Among them, 17 proteins showed increased expression in the exponential phase and 15 were identified by mass spectrometry. Comparison of 2D-PAGE of cytoplasmic proteins showed 20 differentially (by at least 1.5 fold) expressed proteins. Contrary to the membrane proteins, the majority (19) of cytoplasmic proteins showed increased expression during the stationary phase. Only one protein spot, corresponding to flagellin, had higher expression in the exponential phase. The majority of identified proteins were implicated in either anabolic or catabolic processes showing an overall mixt metabolic profile in both growth phases.

ATP Production by *E. coli* Proteins In Vitro

To study if bacterial proteome change during growth phases may influence their energy extraction capacities, the ATP production from nutrients by *E. coli* K12 proteins of the exponential and stationary phases was tested in vitro. We found that proteins from both growth phases were able to increase ATP production from different energy sources. The ATP concentrations were higher when a protein-containing mixed energy source, such as the MH medium, was used as compared to a sucrose solution. The ATP production increased dose-dependently with concentrations of bacterial proteins, however, no significant differences were found between ATP-producing effects of proteins from the exponential or stationary phases.

ClpB Production by E. coli In Vitro

We developed and validated an enzyme-linked immunosorbent assay (ELISA) for detection of E. coli ClpB, which has been used in this study. Whether ClpB protein production is different between bacterial growth phases was studied in 4 separate E. coli K12 cultures. The Western blot detected ClpB-corresponding 96 KDa bands in all proteins preparations with increased levels during the stationary phase. These changes have been further confirmed using the ClpB ELISA in the same bacterial protein preparations, showing that ClpB concentrations almost doubled in the stationary phase.

Intestinal Infusions of Nutrients and E. coli Proteins

To verify if our in vitro model of nutrient-induced E. coli growth is relevant to gut bacterial growth dynamics in vivo, MH medium or water were infused into the colon of anaesthetized rats. We found that instillations of MH medium, but not water, induced bacterial proliferation in the gut with the exponential growth phase lasting for 20 min, consistent with the in vitro data. Plasma ClpB levels measured in the portal vein were not significantly different 30 or 60 min after MH infusion. Nevertheless, plasma ClpB concentrations correlated positively with ClpB DNA content in faeces.

Next, to determine if growth-dependent changes of E. coli proteomes may influence host mechanisms of appetite control locally in the gut, in a separate experiment, anaesthetized rats received 20 min colonic infusions of E. coli proteins from the exponential or stationary phases, both at 0.1 mg/kg. The concentrations of ClpB in the colonic mucosa measured 20 min after the infusion were higher in rats receiving the stationary phase proteins, however, plasma levels of ClpB were not affected by bacterial proteins from either exponential or stationary phases. Consistent with our hypothesis that effects of E. coli proteins on host appetite signaling might depend on the bacterial growth phase, we found that colonic instillations of E. coli proteins from the exponential but not the stationary phase stimulated plasma levels of GLP-1 and, in contrary, increased plasma levels of PYY were detected after infusion of proteins from the stationary but not the exponential phase.

Food Intake and Brain c-Fos after Acute E. coli Proteins Administrations in Rats Because ClpB was present in plasma in all tested rats and mice, it is possible that plasmatic E. coli proteins might influence appetite via their systemic action and that such effects can be different for proteins associated with bacterial growth phases. By testing this possibility in overnight fasted rats, we found that a single intraperitoneal (I.P.) administration (0.1 mg/kg of body weight) of the membrane fraction of E. coli proteins extracted in the stationary phase, decreased 1 h- and 2 h-food intake during refeeding as compared with the control group. In contrast, administration of the cytoplasmic fraction of E. coli proteins (0.1 mg/kg of body weight, I.P.) extracted in the exponential phase increased 4 h food intake during refeeding.

To further investigate if E. coli total proteins may influence spontaneous food intake in a growth phase-dependent way, and to activate central sites such as the ARC, free feeding rats were injected before the onset of the dark phase with bacterial proteins (0.1 mg/kg of body weight, I.P.). Food intake was measured for 2 h following injections, and then the rats were killed for the analysis of c-fos expression in the brain. We found that rats injected with bacterial proteins from the stationary phase ate less than controls, while food intake was not significantly affected by injections of bacterial proteins from the exponential phase.

Two hours after I.P. injections of E. coli proteins to free feeding rats, c-fos expression was immunohistochemically analyzed in the ARC and the ventromedial nucleus (VMN) of the hypothalamus and in the CeA. The increased number of c-fos-positive cells was found in the ARC and VMN of mice receiving bacterial proteins from the stationary phase. The majority of c-fos expressing cells in the ARC contained β-endorphin (Controls, 71.31±12.81%, E. coli exp. phase, 73.56±10.45%, E. coli stat. phase, 80.50±9.68° 0, ANOVA p=0.36), i.e. were identified as anorexigenic POMC neurons. Accordingly, the percentage of remaining c-fos neurons in the ARC did not significantly differ among the groups (Controls, 28.69±12.8100, E. coli exp. phase, 26.44±10.45%, E. coli stat. phase, 19.5±9.68%, ANOVA p=0.36). Although the total numbers of f-endorphin-positive cells were not significantly different among the groups (Controls, 54.82±10.67 cells, E. coli exp. phase, 66.03±11.43 cells, E. coli stat. phase, 66.03±5.06 cells, ANOVA p=0.09), the relative number of activated β-endorphin neurons was increased in rats receiving stationary phase proteins as compared to controls and to rats receiving exponential phase proteins. Furthermore, the number of activated β-endorphin neurons correlated inversely with food intake (Pearson's r=−0.57, p=0.018).

In the CeA, the number of c-fos-positive cells was increased in rats injected with proteins from the stationary phase, as compared to the two other groups. Almost all c-fos-positive cells in the CeA were phenotyped as CGRP-expressing neurons (Controls, 100±0.01%, E. coli exp. phase, 100±0.01%, E. coli stat. phase, 100±0.01%, ANOVA p=0.92). Although the total numbers of CGRP-positive neurons in the CeA were similar among the groups (Controls, 123.8±13.15 cells, E. coli exp. phase, 118.3±25.59 cells, E. coli stat. phase, 126.1±6.64 cells, ANOVA p=0.85), the percentage of c-fos activated CGRP neurons was increased only in rats receiving stationary phase proteins. Activation of CGRP neurons correlated inversely with food intake (Pearson's r=−0.89, p=0.001).

Feeding Pattern and Hypothalamic Neuropeptides after Chronic E. coli Protein Injections in Mice To determine if bacterial proteins may influence feeding pattern, two daily injections of E. coli total proteins (0.1 mg/kg of body weight, I.P.) were administered for one week to free feeding mice. The first day after injections was characterized by significantly lower body weight and food intake in mice receiving bacterial proteins from the stationary but not the exponential phase as compared to controls. Although daily meal size was not significantly different among the groups, its decrease relative to the day before injections was observed one week later in mice receiving stationary phase proteins. Meal frequency was not significantly different among the groups, although a trend towards an increase was observed in mice receiving bacterial proteins from the stationary phase. Although total food intake among 3 groups was not significantly different during 6 days of injections, analyzing it separately for the light and dark periods, showed that mice injected with the exponential phase proteins had increased food intake during the light period, but it was decreased during the dark period. In contrast, mice receiving the stationary phase proteins displayed lower than controls food intake in the dark period without any effect in the light period. During the first day after injections, the satiety ratio was increased in mice receiving proteins from the stationary phase, and the same group showed a tendency towards a decrease, one week later.

To get an insight into the molecular changes underlying altered feeding pattern observed after 6 days of bacterial protein injections, we analyzed hypothalamic mRNA expression levels of several neuropeptides involved in appetite control. We found that mice receiving the stationary phase proteins showed elevated precursor mRNA levels of brain-derived neurotrophic factor (BDNF) and orexin as compared to controls, and of corticotropin-releasing hormone (CRH) as compared to mice injected with proteins in the exponential phase, which also showed elevated levels of BDNF but decreased QRFP.

Electrophysiological Activation of Hypothalamic POMC Neurons by ClpB

To determine whether ClpB, as a marker of E. coli proteins up-regulated in the stationary growth phase and a mimetic of α-MSH, activates ARC POMC neurons, ClpB effect was examined on brain slices from POMC-eGFP mice using cell-attached patch-clamp electrophysiology. Bath application of ClpB (1 nM) increased action potential frequency of ~50% of ARC POMC neurons (n=7/13), by 229±109% (basal: 2.02±0.78 Hz vs. ClpB: 3.82±1.36 Hz). In general, POMC neurons did not fully return to their basal firing rates until at least 10 min after ClpB application.

Discussion

Our study reveals that bacterial proteins may physiologically link gut bacteria to the host control of appetite including its both short- and long-term mechanisms associated with the nutrient-induced bacterial growth in the gut and their systemic effects, respectively. The following main results support this conclusion: 1) regular provision of nutrients accelerates and stabilizes the exponential growth of E. coli lasting for 20 min, in agreement with the in vivo data; 2) E. coli stationary growth phase was characterized by increased total bacterial protein content and a different proteome profile, including increased ClpB; 3) E. coli proteins from both growth phases dose-dependently stimulated in vitro ATP production; 4) Plasma levels of ClpB did not change after nutrient-induced bacterial growth in the gut, but correlated with ClpB DNA in gut microbiota; 5) Intestinal infusion of E. coli proteins from the exponential and stationary growth phases stimulated plasma GLP-1 and PYY, respectively. 6) Systemic injections of E. coli proteins decreased significantly food intake only by the proteins from the stationary phase, accompanied by c-fos activation in anorexigenic ARC and CeA neurons, and finally 7) ClpB stimulated firing rate of ARC POMC neurons.

Regular Provision of Nutrients and Bacterial Growth

Among the wide variety of bacteria that colonize the gastrointestinal tracts of humans, E. coli is the most abundant facultative anaerobe, justifying it as a model organism for commensal gut bacteria (Foucault et al., 2009). Here, we found that E. coli change their dynamics of growth during regular nutrient supply, resulting after the 5$^{th}$ feeding cycle, in an immediate exponential growth lasting for 20 min followed by the stationary phase. The growth cycle is then identically reproduced after the next provision of nutrients, suggesting that it can play a role of a pacemaker set by intrinsic to bacteria mechanisms. A similar dynamics of bacterial growth in response to nutrient infusion was seen in the rat colon, supporting that our in vitro data can be relevant to in vivo situations, e.g. in humans taking regular meals. The $10^8$-$10^9$ increment of bacterial number remained stable after each new provision, suggesting that the corresponding stable production of the bacterial biomass, including increased protein content in the gut, may play a role of a meal-induced regulatory factor for the host. Given that the average prandial phase in humans is similar to the duration of the exponential growth of regularly-fed bacteria, it is tempting to speculate that the host satiety can be triggered by gut bacteria reaching the stationary phase, 20 min after a contact with ingested nutrients. However, bacterial content in the gastrointestinal tract ranges from $10^3$ in the stomach to $10^{12}$ in the colon. Moreover, about 2 h is necessary for the advancement of ingested nutrients through the stomach and small intestine and about 10 h through the large intestine. Because of such a delay of nutrient delivery to most gut bacteria, it is likely that beside the direct contact with the nutrient bolus, bacterial growth during the prandial phase might be also initiated by nutrients released into the gut lumen by the Pavlovian cephalic reflex to ingestion.

Bacterial Protein Expression During Growth Phases and Intestinal Sensing

Because the growth dynamics of regularly-fed E. coli can be associated with the host prandial and postprandial phases, we have studied if expression of bacterial proteins may potentially link gut bacteria and host control of appetite. First, we compared the proteomes of E. coli in the exponential vs. stationary growth phases. For this analysis, E. coli proteins were extracted in the middle of the exponential phase, i.e. 10 min after nutrient provision, and in the stationary phase 2 h later, a time normally characterized by feeling of satiety. The finding of at least 40 differentially expressed proteins between two growth phases confirmed that they differ not only quantitatively, by protein content, which almost doubled after bacterial proliferation, but also qualitatively. The possible relevance of the modified protein expression profile to the host control of appetite has been then studied: i) by comparing the ability of bacterial proteins to generate energy substrate, and ii) by determining possible direct effects of bacterial proteins on appetite-regulatory pathways. The late possibility is supported by the recent proteomic identification of E. coli ClpB as a conformational protein mimetic of α-MSH (Tennoune et al., 2014); the data that validated our earlier hypothesis that gut bacterial proteins, displaying epitopes homologous to anorexigenic or orexigenic peptides, may be responsible for production of cross-reactive autoantibodies (Fetissov et al., 2008). It is, hence, conceivable that a combination of such bacterial mimetic proteins may influence appetite directly, depending on the protein expression profile associated with the bacterial growth phase. By analysing E. coli cultures and the intestinal mucosa, we found increased ClpB levels associated with the stationary growth phase. Increased ClpB may, hence, contribute to the activation of anorexigenic pathways after nutrient-induced E. coli proliferation and increased bacterial protein production. An important question is where the bacterial proteins, such as ClpB, may act on the appetite-regulatory pathways.

Although bacterial proteins are present in the intestinal mucosa (Haange et al., 2012), their passage across the gut barrier has not been extensively studied (Lim and Rowley, 1985). In theory, after spontaneous and induced bacterial lyses in the gut (Rice and Bayles, 2008), bacterial components can pass across the mucosal epithelial barrier by absorption in enterocytes and by paracellular diffusion, regulated by the enteric nervous system (Neunlist et al., 2012). For instance, lipopolysaccharide (LPS), which is released upon lysis of gram-negative bacteria, is naturally present in plasma of healthy humans and mice with higher basal levels after consuming high fat diets (Cani et al., 2007). LPS plasma levels are also increased postprandially (Harte et al., 2012), but there are no such data about bacterial proteins. Here we show that plasma ClpB levels remain stable in rats following bacterial proliferation in the gut or after intestinal infusion of bacterial proteins. It indicates that plasmatic ClpB, and most likely other bacterial proteins present in plasma, are not acutely influenced by nutrient-induced bacterial proliferation, and hence, they cannot be involved in the short-term satiety signaling to the brain.

Nevertheless, plasma ClpB concentrations correlated with ClpB DNA in gut microbiota, suggesting that the number of ClpB-producing bacteria, which should be at long-term relatively independent from its fluctuations related to the nutrient-driven bacterial growth, can be the main factor responsible for the long-term maintenance of plasma ClpB levels. This conclusion is further supported by our data, obtained for validation of ClpB ELISA, showing increased plasma ClpB concentrations in mice chronically gavaged with E. coli but not in mice that received ClpB-mutant E. coli. It is hence, possible that gut bacterial proteins present in plasma, including ClpB, may act systemically linking the composition of gut microbiota with the long-term control of energy metabolism.

Effects of E. coli Proteins on ATP Production In Vitro

Energy exchange through the food chains represents a universal link between all organisms (Yun et al., 2006). ATP, derived from nutrient catabolism in both bacteria and animals, serves as the main energy substrate for anabolic processes. Animals can sense changes in ATP via the activity of adenosine-5'-monophosphate-activated protein kinase (AMPK), resulting in increased food intake, when ATP levels are low and rice versa (Dzamko and Steinberg, 2009). Hence, in the present work, we compared the ability of E. coli proteins in exponential and stationary phases to generate ATP in vitro. Indeed, many of the identified proteins displayed anabolic or catabolic properties. We found that E. coli proteins are able to stimulate ATP-production in vitro, suggesting that they may continue to catalyze ATP production after the bacterial lysis in the gut. Although no differences in ability to produce ATP was found between the proteins from the exponential and stationary phases, the bacterial protein concentration-dependent ATP production indicates that increased bacterial protein content, after nutrient-induced bacterial proliferation, should result in higher ATP synthesis. The relevance of the efficiency of gut microbiota to harvest energy for the host metabolism has been previously established by comparing obese and lean humans and mice (Turnbaugh et al., 2006). Our data further corroborate these results by showing the ability of E. coli proteins to generate ATP. It also suggests that meal-induced bacterial proliferation may lead to increased intestinal ATP, which should contribute to the luminal sensing of energy availability and gut relaxation (Glasgow et al., 1998).

Intestinal Effects of E. coli Proteins on Satiety Hormones

Next, we studied if E. coli proteins in the gut may stimulate the systemic release of gut satiety hormones such as GLP-1 and PYY (Adrian et al., 1985; Batterham et al., 2002; Beglinger and Degen, 2006; Flint et al., 1998). In fact, both hormones are produced by the same or distinct enteroendocrine L-cells present throughout the intestine and abundant in the colon (Eissele et al., 1992), and hence, L-cells are directly exposed to bacterial proteins. We found differential effects of E. coli proteins on GLP- and PYY release, showing stimulation of GLP-1 by the proteins from the exponential and of PYY from the stationary growth phases. These results point to some similarities between nutrient-induced bacterial growth and the known dynamics of meal-induced release of GLP-1 and PYY. In fact, as was shown in humans, an acute peak of plasma GLP-1 occurs 15 min after an intragastric infusion of a liquid meal, while a longer-lasting elevated plasma PYY starts between 15 and 30 min after a meal (Edwards et al., 1999; Gerspach et al., 2011). Longer release of GLP-1 was associated with fat intake (van der Klaauw et al., 2013). Thus, the growth dynamics of regularly-fed gut bacteria fits temporally into the dynamics of GLP-1 and PYY release, suggesting an inductive role of gut bacteria, and specifically of E. coli proteins, in meal-induced signaling of intestinal satiety. A differential effect of E. coli proteins from the exponential phase to stimulate GLP-1, may possibly reflect an incretin role of GLP-1 in glycemic control (Edwards et al., 1999; Steinert et al., 2014). A recent demonstration of functional MC4R expressed by L-cells (Panaro et al., 2014), provide a background for their possible activation by α-MSH-mimetic bacterial proteins. An increased production of ClpB during the E. coli stationary phase, as well as elevated ClpB levels in the intestinal mucosa, associated with increased plasma PYY levels, suggest a direct role of ClpB in activation of PYY-producing L-cells in the colon. From the other hand, so far non-identified E. coli proteins possibly upregulated during the exponential growth phase, may preferentially stimulate GLP-1 secretion.

Systemic Effects of E. coli Proteins on Food Intake and Appetite-Regulating Brain Pathways We showed here that peripheral injections of E. coli proteins to hungry or free-feeding rats and free-feeding mice changed their food intake depending on the growth phase of E. coli. Considering that plasma ClpB was not affected by intestinal infusion of nutrients but was stable over short time, the systemic action of bacterial proteins should be interpreted as relevant to their long-term modulatory effects on appetite. Furthermore, because of a short duration of the exponential phase, bacterial proteins upregulated during the long-lasting stationary phase should dominate in plasma, and hence, their systemic administrations can better represent the physiological situations. The 0.1 mg/kg concentrations of E. coli proteins used in these experiments were similar with the effective satietogenic doses of peptide hormones such as leptin or PYY after peripheral administrations in humans or rodents (Batterham et al., 2002; Halaas et al., 1995; Heymsfield et al., 1999).

An increase of food intake in hungry rats during refeeding in light phase was observed after administration of cytoplasmic proteins from the exponential phase and a decrease by the membrane proteins from the stationary phase. This experiment confirmed that different protein mixtures from the same bacteria are able to increase or decrease food intake by their systemic action. However, in a more physiological setting, by testing effect of total E. coli proteins in free feeding rats in the dark phase, only a decrease in food intake was observed which was induced by proteins from the stationary phase.

Results of repeated injections in free feeding mice further support a role of E. coli proteins to promote negative energy balance. Indeed, first day of bacterial protein injections was accompanied by decreased food intake and body weight, being significant in mice receiving stationary phase proteins and who were also characterized by increased satiety ratio. Although food intake in these mice was normalized thereafter, a progressive decrease of meal size was accompanied by increased meal frequency, most likely as a compensatory mechanism to maintain food intake (Meguid et al., 1998). Additionally, differential effects of *E. coli* proteins were observed during the light and dark phases. Accordingly, the pattern of mRNA expression of appetite-regulating neuropeptides in the hypothalamus showed a mixt response with activation of both anorexigenic and orexigenic pathways. Of note, both groups of mice receiving *E. coli* proteins showed similar increase of BDNF mRNA, an anorexigenic pathway downstream to MC4R in the VMN (Xu et al., 2003). This pathway may underlie a decreased food intake during the dark phase observed in both groups, and which was further accentuated in mice injected with the exponential phase proteins showing lower levels of orexigenic QRFP (Chartrel et al., 2003) and NPY (Herzog, 2003). On the contrary, mice that received bacterial proteins from the stationary phase, displayed an enhanced anorexigenic profile with elevated levels of CRH mRNA, most likely implicating MC4R-expressing PVN neurons (Lu et al., 2003). These changes combined with increased mRNA precursor expression of orexin A that stimulates meal frequency (Baird et al., 2009), may contribute to decreased meal size and satiety ratio, respectively, in these mice after 6 days of injections.

Consistent with our hypothesis that bacterial proteins produced during the stationary phase may activate some key central anorexigenic pathways, we found in free feeding rats an increased c-fos expression in the anorexigenic ARC POMC neurons as well as in the VMN, which has long been known as a satiety center and is interconnected with the ARC POMC neurons (Sternson et al., 2005). The obtained c-fos pattern resembles that of a satietogenic response during food ingestion (Johnstone et al., 2006) or induced by satiety hormones such as PYY or pancreatic polypeptide (Batterham et al., 2002; Challis et al., 2004; Lin et al., 2009). A relatively small number (~10%) of c-fos-activated POMC neurons suggests that circulating *E. coli* proteins might have a modulatory effect on appetite and body weight acting via this hypothalamic pathways. Although it was not feasible to determine c-fos activation by the NPY/AgRP neurons, their contribution to signaling by bacterial proteins cannot be excluded; these neurons also express MC3R and MC4R (Mounien et al., 2005). Moreover, a stronger than in the ARC POMC activations of c-fos in the CeA CGRP neurons (~40%) may signify a convergent down-stream action from ARC POMC and NPY/AgRP neurons and possibly from other appetite-regulating brain areas, which has not been analyzed here, such as the nucleus of the solitary tract.

Finally, to determine if activation of appetite-regulating brain sites, such as the ARC POMC neurons, by bacterial proteins may be caused by their local action, we studied if application of ClpB on these neurons may activate their electrical activity. Our results showed that about a half of studied neurons increased their action potential frequency, remaining activated for at least 10 min. The sustained effect of ClpB is consistent with the effect of α-MSH on POMC neurons expressing functional MC3R and MC4R (Smith et al., 2007), suggesting that ClpB can be a physiological activator of the hypothalamic POMC neurons, somewhat similar to satietogenic PYY and leptin (Batterham et al., 2002; Cowley et al., 2001). However, we do not know if ClpB was able to activate POMC neurons directly or via a local network.

Taken together, these data support a role of systemically present *E. coli* proteins which expression is increased in the stationary growth phase, such as ClpB, in promoting negative energy balance via activation of brain anorexigenic pathways. It also suggests that changes of microbiota composition resulting in low or high abundance of *E. coli*, and possibly of other bacteria from the family of Enterobacteriaceae, may influence the host energy balance in a positive or negative ways, respectively.

EXAMPLE 2

One-month-old male C57Bl6 mice (Janvier Laboratories) were acclimated to the animal facility for 1 week and maintained as described above. Mice were distributed into 3 groups as follows: (i) gavaged with 10' *E. coli* K12 bacteria; (ii) gavaged with 10' *E. coli* K12 bacteria deficient for ClpB; (iii) and controls that did not receive any treatments. The ClpB mutant strain was generated in the Bernd Bukau's Laboratory (ZMBH, Heidelberg University, Heidelberg, Germany) and was kindly provided together with the corresponding wildtype (WT) *E. coli* bacteria 5 by Dr Axel Mogk. Mice were placed individually into the BioDAQ cages (Research Diets) and intragastrically gavaged daily before the onset of dark phase for 21 days with 0.5 ml of LB medium with the bacteria. The first days of gavage were accompanied by a decrease in body weight and food intake in mice receiving WT *E. coli*, contrary to the bacteria that do not express the ClpB protein (FIG. 1).

REFERENCES

Throughout this application, various references describe the state of the art to which this invention pertains. The disclosures of these references are hereby incorporated by reference into the present disclosure.

Adrian, T. E., Ferri, G. L., Bacarese-Hamilton, A. J., Fuessl, H. S., Polak, J. M., and Bloom, S. R. (1985). Human distribution and release of a putative new gut hormone, peptide YY. Gastroenterology 89, 1070-1077.

Atasoy, D., Betley, J. N., Su, H. H., and Sternson, S. M. (2012). Deconstruction of a neural circuit for hunger. Nature 488, 172-177.

Baird, J.-P., Choe, A., Loveland, J. L., Beck, J., Mahoney, C. E., Lord, J. S., and Grigg, L. A. (2009). Orexin-A hyperphagia: hindbrain participation in consummatory feeding responses. Endocrinology 150, 1202-1216.

Batterham, R. L., Cowley, M. A., Small, C. J., Herzog, H., Cohen, M. A., Dakin, C. L., Wren, A. M., Brynes, A. E., Low, M. J., Ghatei, M. A., et al. (2002). Gut hormone PYY(3-36) physiologically inhibits food intake. Nature 418, 650-654.

Beglinger, C., and Degen, L. (2006). Gastrointestinal satiety signals in humans—Physiologic roles for GLP-1 and PYY ? Physiology & Behavior 89, 460-464.

Berthoud, H.-R. (2011). Metabolic and hedonic drives in the neural control of appetite: who is the boss? Current Opinion in Neurobiology 21, 888-896.

Cani, P. D., Amar, J., Iglesias, M. A., Poggi, M., Knauf, C., Bastelica, D., Neyrinck, A. M., Fava, F., Tuohy, K. M., Chabo, C., et al (2007). Metabolic endotoxemia initiates obesity and insulin resistance. Diabetes 56, 1761-1772.

Carter, M. E., Soden, M. E., Zweifel, L. S., and Palmiter, R. D. (2013). Genetic identification of a neural circuit that suppresses appetite. Nature 503, 111-114.

Challis, B. G., Coll, A. P., Yeo, G. S. H., Pinnock, S. B., Dickson, S. L., Thresher, R. R., Dixon, J., Zahn, D., Rochford, J. J., White, A., et al. (2004). Mice lacking proopiomelanocortin are sensitive to high-fat feeding but respond normally to the acute anorectic effects of peptide-YY3-36. Proc. Natl. Acad. Sci. USA 101, 4695-4700.

Chartrel, N., Dujardin, C., Anouar, Y., Leprince, J., Decker, A., Clerens, S., Do-Rego, J. C., Vandesande, F., Llorens- Cortes, C., Costentin, J., et al. (2003). Identification of 26RFa, a hypothalamic neuropeptide of the RFamide peptide family with orexigenic activity. Proc Natl Acad Sci USA 100, 15247-15252.

Cone, R. D. (2005). Anatomy and regulation of the central melanocortin system. Nat Neurosci 8, 571-578.

Cowley, M. A., Pronchuk, N., Fan, W., Dinulescu, D. M., Colmers, W. F., and Cone, R. D. (1999). Integration of NPY, AGRP, and melanocortin signals in the hypothalamic paraventricular nucleus: evidence of a cellular basis for the adipostat. Neuron 24, 155-163.

Cowley, M. A., Smart, J. L., Rubinstein, M., Cerdan, M. G., Diano, S., Horvath, T. L., Cone, R. D., and Low, M. J. (2001). Leptin activates anorexigenic POMC neurons through a neural network in the arcuate nucleus. Nature 411, 480-484.

Dinan, T. G., Stilling, R. M., Stanton, C., and Cryan, J. F. (2015). Collective unconscious: How gut microbes shape human behavior. Journal of Psychiatric Research 63, 1-9.

Dzamko, N. L., and Steinberg, G. R. (2009). AMPK-dependent hormonal regulation of whole-body energy metabolism. Acta Physiologica 196, 115-127.

Edwards, C. M., Todd, J. F., Mahmoudi, M., Wang, Z., Wang, R. M., Ghatei, M. A., and Bloom, S. R. (1999). Glucagon-like peptide 1 has a physiological role in the control of postprandial glucose in humans: studies with the antagonist exendin 9-39. Diabetes 48, 86-93.

Eissele, R., Goke, R., Willemer, S., Harthus, H. P., Vermeer, H., Arnold, R., and Goke, B. (1992). Glucagon-like peptide-1 cells in the gastrointestinal tract and pancreas of rat, pig and man. European journal of clinical investigation 22, 283-291.

Fetissov, S. O., and Déchelotte, P. (2011). The new link between gut-brain axis and neuropsychiatric disorders. Curr Opin Clin Nutr Metab Care 14, 477-482.

Fetissov, S. O., Hamze Sinno, M., Coëffier, M., Bole-Feysot, C., Ducrotté, P., Hökfelt, T., and Déchelotte, P. (2008). Autoantibodies against appetite-regulating peptide hormones and neuropeptides: putative modulation by gut microflora. Nutrition 24, 348-359.

Fioramonti, X., Contie, S., Song, Z., Routh, V. H., Lorsignol, A., and Penicaud, L. (2007). Characterization of glucosensing neuron subpopulations in the arcuate nucleus: integration in neuropeptide Y and pro-opio melanocortin networks? Diabetes 56, 1219-1227.

Flint, A., Raben, A., Astrup, A., and Hoist, J. J. (1998). Glucagon-like peptide 1 promotes satiety and suppresses energy intake in humans. The Journal of Clinical Investigation 101, 515-520.

Forsythe, P., and Kunze, W. (2013). Voices from within: gut microbes and the CNS. Cellular and Molecular Life Sciences 70, 55-69.

Foucault, M.-L., Thomas, L., Goussard, S., Branchini, B. R., and Grillot-Courvalin, C. (2009). In vivo bioluminescence imaging for the study of intestinal colonization by *Escherichia coli* in mice. Applied and Environmental Microbiology 76, 264-274.

Garfield, A. S., Li, C., Madara, J. C., Shah, B. P., Webber, E., Steger, J. S., Campbell, J. N., Gavrilova, O., Lee, C. E., Olson, D. P., et al. (2015). A neural basis for melanocortin-4 receptor-regulated appetite. Nat Neurosci doi: 10.1038/nn.4011.

Gerspach, A. C., Steinert, R. E., Schönenberger, L., Graber-Maier, A., and Beglinger, C. (2011). The role of the gut sweet taste receptor in regulating GLP-1, PYY, and CCK release in humans. Am J Physiol Endocrinol Metab 301, E317-E325.

Glasgow, I., Mattar, K., and Krantis, A. (1998). Rat gastroduodenal motility in vivo: involvement of NO and ATP in spontaneous motor activity. Am. J. Physiol. Gastrointest. Liver Physiol 275, G889-G896.

Goichon, A., Coëffier, M., Claeyssens, S., Lecleire, S., Cailleux, A.-F., Bole-Feysot, C., Chan, P., Donnadieu, N., Lerebours, E., Lavoinne, A., et al. (2011). Effects of an enteral glucose supply on protein synthesis, proteolytic pathways, and proteome in human duodenal mucosa. The American Journal of Clinical Nutrition 94, 784-794.

Haange, S. B., Oberbach, A., Schlichting, N., Hugenholtz, F., Smidt, H., von Bergen, M., Till, H., and Seifert, J. (2012). Metaproteome analysis and molecular genetics of rat intestinal microbiota reveals section and localization resolved species distribution and enzymatic functionalities. J Proteome Res 11, 5406-5417.

Halaas, J. L., Gajiwala, K. S., Maffei, M., Cohen, S. L., Chait, B. T., Rabinowitz, D., Lallone, R. L., Burley, S. K., and Friedman, J. M. (1995). Weight-reducing effects of the plasma protein encoded by the obese gene. Science 269, 543-546.

Harte, A. L., Varma, M. C., Tripathi, G., McGee, K. C., Al-Daghri, N. M., Al-Attas, O. S., Sabico, S., O'Hare, J. P., Ceriello, A., Saravanan, P., et al. (2012). High fat intake leads to acute postprandial exposure to circulating endotoxin in type 2 diabetic subjects. Diabetes Care 35, 375-382.

Herzog, H. (2003). Neuropeptide Y and energy homeostasis: insights from Y receptor knockout models. Eur J Pharmacol 480, 21-29.

Heymsfield, S. B., Greenberg, A. S., Fujioka, K., Dixon, R. M., Kushner, R., Hunt, T., Lubina, J. A., Patane, J., Self, B., Hunt, P., et al. (1999). Recombinant leptin for weight loss in obese and lean adults: A randomized, controlled, dose-escalation trial. JAMA 282, 1568-1575.

Inui, A. (1999). Feeding and body-weight regulation by hypothalamic neuropeptides-mediation of the actions of leptin. Trends Neurosci 22, 62-67.

Johnstone, L. E., Fong, T. M., and Leng, G. (2006). Neuronal activation in the hypothalamus and brainstem during feeding in rats. Cell Metabolism 4, 313-321.

Ley, R. E., Turnbaugh, P. J., Klein, S., and Gordon, J. I. (2006). Microbial ecology: Human gut microbes associated with obesity. Nature 444, 1022-1023.

Lim, P. L., and Rowley, D. (1985). Intestinal absorption of bacterial antigens in normal adult mice. II. A comparative study of techniques. Int Arch Allergy Appl Immunol 76, 30-36.

Lin, S., Shi, Y.-C., Yulyaningsih, E., Aljanova, A., Zhang, L., Macia, L., Nguyen, A. D., Lin, E.-J. D., During, M. J., Herzog, H., et al. (2009). Critical role of arcuate Y4 receptors and the melanocortin system in pancreatic polypeptide-induced reduction in food intake in mice. PLoS One 4, e8488.

Lu, X. Y., Barsh, G. S., Akil, H., and Watson, S. J. (2003). Interaction between alpha-melanocyte-stimulating hormone and corticotropin-releasing hormone in the regulation of feeding and hypothalamo-pituitary-adrenal responses. J Neurosci 23, 7863-7872.

Manning, S., and Batterham, Rachel L. (2014). Enteroendocrine MC4R and energy balance: linking the long and the short of it. Cell Metabolism 20, 929-931.

Meguid, M. M., Laviano, A., and Rossi-Fanelli, F. (1998). Food intake equals meal size times mean number. Appetite 31, 404.

Mounien, L., Bizet, P., Boutelet, I., Vaudry, H., and Jégou, S. (2005). Expression of melanocortin MC3 and MC4 receptor mRNAs by neuropeptide Y neurons in the rat arcuate nucleus. Neuroendocrinology 82, 164-170.

Mul, J. D., Spruijt, B. M., Brakkee, J. H., and Adan, R. A. H. (2013). Melanocortin MC4 receptor-mediated feeding and grooming in rodents. European Journal of Pharmacology 719, 192-201.

Murphy, K. G., and Bloom, S. R. (2006). Gut hormones and the regulation of energy homeostasis. Nature 444, 854-859.

Neunlist, M., Van Landeghem, L., Mahe, M. M., Derkinderen, P., Bruley des Varannes, S. B., and Rolli-Derkinderen, M. (2012). The digestive neuronal-glial-epithelial unit: a new actor in gut health and disease. Nat Rev Gastroenterol Hepatol 10, 90-100.

Panaro, B. L., Tough, I. R., Engelstoft, M. S., Matthews, R. T., Digby, G. J., Moller, C. L., Svendsen, B., Gribble, F., Reimann, F., Hoist, J. J., et al. (2014). The melanocortin-4 receptor is expressed in enteroendocrine L cells and regulates the release of peptide YY and glucagon-like peptide 1 in vivo. Cell Metab 20, 1018-1029.

Parks, B. W., Nam, E., Org, E., Kostem, E., Norheim, F., Hui, S. T., Pan, C., Civelek, M., Rau, C. D., Bennett, B. J., et al. (2013). Genetic control of obesity and gut microbiota composition in response to high-fat, high-sucrose diet in mice. Cell Metabolism 17, 141-152.

Power, M. L., and Schulkin, J. (2008). Anticipatory physiological regulation in feeding biology: Cephalic phase responses. Appetite 50, 194-206.

Rice, K. C., and Bayles, K. W. (2008). Molecular control of bacterial death and lysis. Microbiology and Molecular Biology Reviews 72, 85-109.

Sharon, G., Garg, N., Debelius, J., Knight, R., Dorrestein, Pieter C., and Mazmanian, Sarkis K. (2014). Specialized metabolites from the microbiome in health and disease. Cell Metabolism 20, 719-730.

Shi, Y.-C., Lau, J., Lin, Z., Zhang, H., Zhai, L., Sperk, G., Heilbronn, R., Mietzsch, M., Weger, S., Huang, X.-F., et al. (2013). Arcuate NPY controls sympathetic output and BAT function via a relay of tyrosine hydroxylase neurons in the PVN. Cell Metabolism 17, 236-248.

Smith, M. A., Hisadome, K., Al-Qassab, H., Heffron, H., Withers, D. J., and Ashford, M. L. (2007). Melanocortins and agouti-related protein modulate the excitability of two arcuate nucleus neuron populations by alteration of resting potassium conductances. J Physiol 578, 425-438.

Steinert, R. E., Schirra, J., Meyer-Gerspach, A. C., Kienle, P., Fischer, H., Schulte, F., Goeke, B., and Beglinger, C. (2014). Effect of glucagon-like peptide-1 receptor antagonism on appetite and food intake in healthy men. The American Journal of Clinical Nutrition 100, 514-523.

Sternson, S. M., Shepherd, G. M. G., and Friedman, J. M. (2005). Topographic mapping of VMH—arcuate nucleus microcircuits and their reorganization by fasting. Nat Neurosci 8, 1356-1363.

Takagi, K., Legrand, R., Asakawa, A., Amitani, H., Francois, M., Tennoune, N., Coëffier, M., Claeyssens, S., do Rego, J.-C., Déchelotte, P., et al. (2013). Anti-ghrelin immunoglobulins modulate ghrelin stability and its orexigenic effect in obese mice and humans. Nat Commun 4:2685.

Tennoune, N., Chan, P., Breton, J., Legrand, R., Chabane, Y. N., Akkermann, K., Jarv, A., Ouelaa, W., Takagi, K., Ghouzali, I., et al. (2014). Bacterial ClpB heat-shock protein, an antigen-mimetic of the anorexigenic peptide [alpha]-MSH, at the origin of eating disorders. Transl Psychiatry 4, e458.

Tennoune, N., Legrand, R., Ouelaa, W., Breton, J., Lucas, N., Bole-Feysot, C., Rego, J.-C. d., Déchelotte, P., and Fetissov, S. O. (2015). Sex-related effects of nutritional supplementation of Escherichia coli: Relevance to eating disorders. Nutrition 31, 498-507.

Turnbaugh, P. J., Ley, R. E., Mahowald, M. A., Magrini, V., Mardis, E. R., and Gordon, J. I. (2006). An obesity-associated gut microbiome with increased capacity for energy harvest. Nature 444, 1027-1131.

van der Klaauw, A. A., Keogh, J. M., Henning, E., Trowse, V. M., Dhillo, W. S., Ghatei, M. A., and Farooqi, I. S. (2013). High protein intake stimulates postprandial GLP1 and PYY release. Obesity 21, 1602-1607.

Vijay-Kumar, M., Aitken, J. D., Carvalho, F. A., Cullender, T. C., Mwangi, S., Srinivasan, S., Sitaraman, S. V., Knight, R., Ley, R. E., and Gewirtz, A. T. (2010). Metabolic syndrome and altered gut microbiota in mice lacking toll-like receptor 5. Science 328, 228-231.

Wick, L. M., Quadroni, M., and Egli, T. (2001). Short- and long-term changes in proteome composition and kinetic properties in a culture of Escherichia coli during transition from glucose-excess to glucose-limited growth conditions in continuous culture and vice versa. Environ Microbiol 3, 588-599.

Xu, B., Goulding, E. H., Zang, K., Cepoi, D., Cone, R. D., Jones, K. R., Tecott, L. H., and Reichardt, L. F. (2003). Brain-derived neurotrophic factor regulates energy balance downstream of melanocortin-4 receptor. Nat Neurosci 6, 736-742.

Yun, A. J., Lee, P. Y., Doux, J. D., and Conley, B. R. (2006). A general theory of evolution based on energy efficiency: its implications for diseases. Medical Hypotheses 66, 664-670.

The invention claimed is:

1. A method of stimulating weight loss in a subject in need thereof comprising orally administering to the subject an effective amount of a ClpB consisting of the amino acid sequence SEQ ID NO:1.

2. The method of claim 1, wherein the subject is obese.

3. The method of claim 1, wherein the subject the subject is not obese.

4. The method of claim 1, wherein the ClpB protein is administered to the subject in the form of a pharmaceutical composition.

5. The method of claim 4, wherein the pharmaceutical composition is a sustained-release pharmaceutical composition.

6. The method of claim 4, wherein the pharmaceutical composition is a gastro-resistant pharmaceutical composition.

7. The method of claim 1, wherein the ClpB protein is administered to the subject in the form of a food composition.

8. The method of claim 7, wherein the food composition is selected from complete food compositions, food supplements and nutraceutical compositions.

9. The method of claim 7, wherein the food composition comprises an amount of dietary fibers.

10. The method of claim 7, wherein the food composition comprises at least one prebiotic.

11. The method of claim 1, wherein the ClpB protein is administered simultaneously or sequentially with one meal of the subject.

12. The method of claim 1, wherein the ClpB protein is administered prior to the subject's meal.

13. The method of claim 1, wherein the method induces satiation and/or prolongs satiety in the subject.

14. The method of claim 13, wherein satiation is induced in the subject, and wherein satiation reduces the meal size and/or the food intake of the subject.

15. The method of claim 1, wherein the ClpB is from a genetically engineered bacterium so as to express said ClpB or from a bacterium subjected to stress conditions so as to up regulate the ClpB protein expression.

* * * * *

SEQUENCE LISTING

```
<160> NUMBER OF SEQ ID NOS: 2

<210> SEQ ID NO 1
<211> LENGTH: 857
<212> TYPE: PRT
<213> ORGANISM: Escherichia coli

<400> SEQUENCE: 1

Met Arg Leu Asp Arg Leu Thr Asn Lys Phe Gln Leu Ala Leu Ala Asp
1               5                   10                  15

Ala Gln Ser Leu Ala Leu Gly His Asp Asn Gln Phe Ile Glu Pro Leu
            20                  25                  30

His Leu Met Ser Ala Leu Leu Asn Gln Glu Gly Gly Ser Val Ser Pro
```

```
                35                  40                  45
Leu Leu Thr Ser Ala Gly Ile Asn Ala Gly Gln Leu Arg Thr Asp Ile
    50                  55                  60
Asn Gln Ala Leu Asn Arg Leu Pro Gln Val Glu Gly Thr Gly Gly Asp
65                  70                  75                  80
Val Gln Pro Ser Gln Asp Leu Val Arg Val Leu Asn Leu Cys Asp Lys
                85                  90                  95
Leu Ala Gln Lys Arg Gly Asp Asn Phe Ile Ser Ser Glu Leu Phe Val
                100                 105                 110
Leu Ala Ala Leu Glu Ser Arg Gly Thr Leu Ala Asp Ile Leu Lys Ala
                115                 120                 125
Ala Gly Ala Thr Thr Ala Asn Ile Thr Gln Ala Ile Glu Gln Met Arg
    130                 135                 140
Gly Gly Glu Ser Val Asn Asp Gln Gly Ala Glu Asp Gln Arg Gln Ala
145                 150                 155                 160
Leu Lys Lys Tyr Thr Ile Asp Leu Thr Glu Arg Ala Glu Gln Gly Lys
                165                 170                 175
Leu Asp Pro Val Ile Gly Arg Asp Glu Glu Ile Arg Arg Thr Ile Gln
                180                 185                 190
Val Leu Gln Arg Arg Thr Lys Asn Asn Pro Val Leu Ile Gly Glu Pro
            195                 200                 205
Gly Val Gly Lys Thr Ala Ile Val Glu Gly Leu Ala Gln Arg Ile Ile
    210                 215                 220
Asn Gly Glu Val Pro Glu Gly Leu Lys Gly Arg Arg Val Leu Ala Leu
225                 230                 235                 240
Asp Met Gly Ala Leu Val Ala Gly Ala Lys Tyr Arg Gly Glu Phe Glu
                245                 250                 255
Glu Arg Leu Lys Gly Val Leu Asn Asp Leu Ala Lys Gln Glu Gly Asn
                260                 265                 270
Val Ile Leu Phe Ile Asp Glu Leu His Thr Met Val Gly Ala Gly Lys
            275                 280                 285
Ala Asp Gly Ala Met Asp Ala Gly Asn Met Leu Lys Pro Ala Leu Ala
    290                 295                 300
Arg Gly Glu Leu His Cys Val Gly Ala Thr Thr Leu Asp Glu Tyr Arg
305                 310                 315                 320
Gln Tyr Ile Glu Lys Asp Ala Ala Leu Glu Arg Arg Phe Gln Lys Val
                325                 330                 335
Phe Val Ala Glu Pro Ser Val Glu Asp Thr Ile Ala Ile Leu Arg Gly
                340                 345                 350
Leu Lys Glu Arg Tyr Glu Leu His His His Val Gln Ile Thr Asp Pro
            355                 360                 365
Ala Ile Val Ala Ala Ala Thr Leu Ser His Arg Tyr Ile Ala Asp Arg
    370                 375                 380
Gln Leu Pro Asp Lys Ala Ile Asp Leu Ile Asp Glu Ala Ala Ser Ser
385                 390                 395                 400
Ile Arg Met Gln Ile Asp Ser Lys Pro Glu Glu Leu Asp Arg Leu Asp
                405                 410                 415
Arg Arg Ile Ile Gln Leu Lys Leu Glu Gln Gln Ala Leu Met Lys Glu
                420                 425                 430
Ser Asp Glu Ala Ser Lys Lys Arg Leu Asp Met Leu Asn Glu Glu Leu
            435                 440                 445
Ser Asp Lys Glu Arg Gln Tyr Ser Glu Leu Glu Glu Glu Trp Lys Ala
            450                 455                 460
```

Glu Lys Ala Ser Leu Ser Gly Thr Gln Thr Ile Lys Ala Glu Leu Glu
465                 470                 475                 480

Gln Ala Lys Ile Ala Ile Glu Gln Ala Arg Val Gly Asp Leu Ala
                485                 490                 495

Arg Met Ser Glu Leu Gln Tyr Gly Lys Ile Pro Glu Leu Glu Lys Gln
            500                 505                 510

Leu Glu Ala Ala Thr Gln Leu Glu Gly Lys Thr Met Arg Leu Leu Arg
            515                 520                 525

Asn Lys Val Thr Asp Ala Glu Ile Ala Glu Val Leu Ala Arg Trp Thr
530                 535                 540

Gly Ile Pro Val Ser Arg Met Met Glu Ser Arg Glu Lys Leu Leu
545                 550                 555                 560

Arg Met Glu Gln Glu Leu His His Arg Val Ile Gly Gln Asn Glu Ala
            565                 570                 575

Val Asp Ala Val Ser Asn Ala Ile Arg Arg Ser Arg Ala Gly Leu Ala
            580                 585                 590

Asp Pro Asn Arg Pro Ile Gly Ser Phe Leu Phe Leu Gly Pro Thr Gly
            595                 600                 605

Val Gly Lys Thr Glu Leu Cys Lys Ala Leu Ala Asn Phe Met Phe Asp
610                 615                 620

Ser Asp Glu Ala Met Val Arg Ile Asp Met Ser Glu Phe Met Glu Lys
625                 630                 635                 640

His Ser Val Ser Arg Leu Val Gly Ala Pro Pro Gly Tyr Val Gly Tyr
                645                 650                 655

Glu Glu Gly Gly Tyr Leu Thr Glu Ala Val Arg Arg Arg Pro Tyr Ser
            660                 665                 670

Val Ile Leu Leu Asp Glu Val Glu Lys Ala His Pro Asp Val Phe Asn
            675                 680                 685

Ile Leu Leu Gln Val Leu Asp Asp Gly Arg Leu Thr Asp Gly Gln Gly
            690                 695                 700

Arg Thr Val Asp Phe Arg Asn Thr Val Val Ile Met Thr Ser Asn Leu
705                 710                 715                 720

Gly Ser Asp Leu Ile Gln Glu Arg Phe Gly Glu Leu Asp Tyr Ala His
                725                 730                 735

Met Lys Glu Leu Val Leu Gly Val Val Ser His Asn Phe Arg Pro Glu
            740                 745                 750

Phe Ile Asn Arg Ile Asp Glu Val Val Phe His Pro Leu Gly Glu
            755                 760                 765

Gln His Ile Ala Ser Ile Ala Gln Ile Gln Leu Lys Arg Leu Tyr Lys
            770                 775                 780

Arg Leu Glu Glu Arg Gly Tyr Glu Ile His Ile Ser Asp Glu Ala Leu
785                 790                 795                 800

Lys Leu Leu Ser Glu Asn Gly Tyr Asp Pro Val Tyr Gly Ala Arg Pro
            805                 810                 815

Leu Lys Arg Ala Ile Gln Gln Ile Glu Asn Pro Leu Ala Gln Gln
            820                 825                 830

Ile Leu Ser Gly Glu Leu Val Pro Gly Lys Val Ile Arg Leu Glu Val
            835                 840                 845

Asn Glu Asp Arg Ile Val Ala Val Gln
850                 855

<210> SEQ ID NO 2
<211> LENGTH: 13

```
<212> TYPE: PRT
<213> ORGANISM: Homo sapiens

<400> SEQUENCE: 2

Ser Tyr Ser Met Glu His Phe Arg Trp Gly Lys Pro Val
1               5                   10
```